(12) United States Patent
Wallace et al.

(10) Patent No.: US 11,896,251 B2
(45) Date of Patent: Feb. 13, 2024

(54) INVERTING THROMBECTOMY APPARATUSES AND METHODS OF USE

(71) Applicant: STRYKER CORPORATION, Fremont, CA (US)

(72) Inventors: Michael P. Wallace, Pleasanton, CA (US); E. Skott Greenhalgh, Gladwyne, PA (US)

(73) Assignee: STRYKER CORPORATION, Fremont, CA (US)

( * ) Notice: Subject to any disclaimer, the term of this patent is extended or adjusted under 35 U.S.C. 154(b) by 94 days.

(21) Appl. No.: 17/387,959

(22) Filed: Jul. 28, 2021

(65) Prior Publication Data

US 2021/0353316 A1 Nov. 18, 2021

Related U.S. Application Data

(63) Continuation of application No. 16/410,946, filed on May 13, 2019, now Pat. No. 11,103,265.

(Continued)

(51) Int. Cl.
*A61B 17/221* (2006.01)
*A61B 17/00* (2006.01)
(Continued)

(52) U.S. Cl.
CPC ...... *A61B 17/221* (2013.01); *A61B 17/00234* (2013.01); *A61B 2017/00292* (2013.01);
(Continued)

(58) Field of Classification Search
CPC ............ A61B 17/221; A61B 17/00234; A61B 2017/00292; A61B 2017/00349;
(Continued)

(56) References Cited

U.S. PATENT DOCUMENTS 3,515,137 A 6/1970 Santomieri
4,222,380 A 9/1980 Terayama
(Continued)

FOREIGN PATENT DOCUMENTS

AU 2015210338 8/2015
CN 201079423 7/2008
(Continued)

OTHER PUBLICATIONS

Foreign OA for CN Patent Appln. No. 201780067034.4 dated Sep. 3, 2021 (with English translation).
(Continued)

*Primary Examiner* — Kelly J Bekker
*Assistant Examiner* — Mohammed S Adam
(74) *Attorney, Agent, or Firm* — Seager, Tufte & Wickhem, LLP

(57) ABSTRACT

Inverting tube thrombectomy apparatus for removing clot that are configured to prevent compression of the apparatus that may separate the distal end of the apparatus from the clot and may make it difficult to advance the apparatus to engage with the clot, particularly in a tortious vessel. The apparatuses and methods of using them described herein may be adapted to prevent tension in the flexible tube that is rolling and inverting over the distal end of the inversion support catheter when capturing a clot. Also described herein are inverting tube thrombectomy apparatus that are configured to reload either automatically or manually within the vessel to capture additional clot material.

15 Claims, 20 Drawing Sheets

Related U.S. Application Data

(60) Provisional application No. 62/671,143, filed on May 14, 2018.

(51) Int. Cl.
*A61B 17/22* (2006.01)
*A61B 17/34* (2006.01)

(52) U.S. Cl.
CPC .............. *A61B 2017/00349* (2013.01); *A61B 2017/00778* (2013.01); *A61B 2017/22038* (2013.01); *A61B 2017/3435* (2013.01)

(58) Field of Classification Search
CPC ........... A61B 2017/00778; A61B 2017/22038; A61B 17/22031; A61B 17/22032; A61M 25/1006
See application file for complete search history.

(56) References Cited

U.S. PATENT DOCUMENTS

| | | |
|---|---|---|
| 4,243,040 A | 1/1981 | Beecher |
| 4,324,262 A | 4/1982 | Hall |
| 4,469,100 A | 9/1984 | Hardwick |
| 4,604,094 A | 8/1986 | Shook |
| 4,646,736 A | 3/1987 | Auth |
| 4,863,440 A | 9/1989 | Chin |
| 4,946,440 A | 8/1990 | Hall |
| 5,011,488 A | 4/1991 | Ginsburg |
| 5,329,923 A | 7/1994 | Lundquist |
| 5,364,345 A | 11/1994 | Lowery et al. |
| 5,389,100 A | 2/1995 | Bacich et al. |
| 5,662,703 A | 9/1997 | Yurek et al. |
| 5,971,938 A | 10/1999 | Hart et al. |
| 6,156,055 A | 12/2000 | Ravenscroft |
| 6,221,006 B1 | 4/2001 | Dubrul et al. |
| 6,238,412 B1 | 5/2001 | Dubrul et al. |
| 6,245,078 B1 | 6/2001 | Ouchi |
| 6,258,115 B1 | 7/2001 | Dubrul |
| 6,544,278 B1 | 4/2003 | Vrba et al. |
| 6,569,181 B1 | 5/2003 | Burns |
| 6,620,179 B2 | 9/2003 | Brook et al. |
| 6,635,068 B1 | 10/2003 | Dubrul et al. |
| 6,635,070 B2 | 10/2003 | Leeflang et al. |
| 6,830,561 B2 | 12/2004 | Jansen et al. |
| 6,846,029 B1 | 1/2005 | Ragner et al. |
| 6,942,682 B2 | 9/2005 | Vrba et al. |
| 7,621,870 B2 | 11/2009 | Berrada et al. |
| 7,780,696 B2 | 8/2010 | Daniel et al. |
| 8,057,496 B2 | 11/2011 | Fischer, Jr. |
| 8,070,769 B2 | 12/2011 | Broome |
| 8,092,486 B2 | 1/2012 | Berrada et al. |
| 8,657,867 B2 | 2/2014 | Dorn et al. |
| 8,721,714 B2 | 5/2014 | Kelley |
| 8,784,442 B2 | 7/2014 | Jones et al. |
| 8,795,305 B2 | 8/2014 | Martin et al. |
| 8,956,384 B2 | 2/2015 | Berrada et al. |
| 9,028,401 B1 | 5/2015 | Bacich et al. |
| 9,125,683 B2 | 9/2015 | Farhangnia et al. |
| 9,126,016 B2 | 9/2015 | Fulton |
| 9,155,552 B2 | 10/2015 | Ulm, III |
| 9,173,668 B2 | 11/2015 | Ulm, III |
| 9,186,487 B2 | 11/2015 | Dubrul et al. |
| 9,358,037 B2 | 1/2016 | Farhangnia et al. |
| 9,259,237 B2 | 2/2016 | Quick et al. |
| 9,351,747 B2 | 5/2016 | Kugler et al. |
| 9,463,035 B1 | 10/2016 | Greenhalgh et al. |
| 9,643,035 B2 | 5/2017 | Mastenbroek |
| 9,717,514 B2 | 8/2017 | Martin et al. |
| 9,848,975 B2 | 12/2017 | Hauser |
| 9,849,014 B2 | 12/2017 | Kusleika |
| 9,962,178 B2 | 5/2018 | Greenhalgh et al. |
| 10,010,335 B2 | 7/2018 | Greenhalgh et al. |
| 10,016,266 B2 | 7/2018 | Hauser |
| 10,028,759 B2 | 7/2018 | Wallace et al. |
| 10,130,385 B2 | 11/2018 | Farhangnia et al. |
| 10,271,864 B2 | 4/2019 | Greenhalgh et al. |
| 10,327,883 B2 | 6/2019 | Yachia |
| 2002/0032455 A1 | 3/2002 | Boock et al. |
| 2002/0035373 A1 | 3/2002 | Carlson et al. |
| 2002/0173819 A1 | 11/2002 | Leeflang et al. |
| 2003/0083693 A1 | 5/2003 | Daniel et al. |
| 2003/0135258 A1 | 7/2003 | Andreas et al. |
| 2003/0153873 A1 | 8/2003 | Luther et al. |
| 2003/0168068 A1 | 9/2003 | Poole et al. |
| 2003/0176884 A1 | 9/2003 | Berrada et al. |
| 2003/0208224 A1 | 11/2003 | Broome |
| 2004/0098033 A1 | 5/2004 | Leeflang et al. |
| 2004/0153110 A1* | 8/2004 | Kurz .................. A61B 17/221 606/159 |
| 2004/0199202 A1 | 10/2004 | Dubrul et al. |
| 2005/0085826 A1 | 4/2005 | Nair et al. |
| 2005/0085849 A1 | 4/2005 | Sepetka et al. |
| 2005/0119668 A1 | 6/2005 | Teague et al. |
| 2005/0177132 A1 | 8/2005 | Lentz et al. |
| 2005/0187570 A1 | 8/2005 | Nguyen et al. |
| 2005/0245876 A1 | 11/2005 | Khosravi et al. |
| 2005/0283166 A1 | 12/2005 | Greenhalgh |
| 2005/0283186 A1 | 12/2005 | Berrada et al. |
| 2006/0042786 A1 | 3/2006 | West |
| 2006/0089533 A1 | 4/2006 | Ziegler et al. |
| 2006/0100662 A1 | 5/2006 | Daniel et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0276874 A1 | 12/2006 | Wilson et al. |
| 2006/0293696 A1 | 12/2006 | Fahey et al. |
| 2007/0112374 A1 | 5/2007 | Paul et al. |
| 2007/0123798 A1 | 5/2007 | Rahimimov |
| 2007/0149996 A1 | 6/2007 | Coughlin |
| 2007/0213765 A1 | 9/2007 | Adams et al. |
| 2008/0183136 A1 | 7/2008 | Lenker et al. |
| 2009/0076417 A1 | 3/2009 | Jones |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0137846 A1 | 6/2010 | Desai |
| 2010/0190156 A1 | 7/2010 | Van Wordragen et al. |
| 2010/0249815 A1 | 9/2010 | Jantzen et al. |
| 2011/0034987 A1 | 2/2011 | Kennedy |
| 2011/0118817 A1 | 5/2011 | Gunderson et al. |
| 2011/0160763 A1 | 6/2011 | Ferrera et al. |
| 2011/0265681 A1 | 11/2011 | Allen et al. |
| 2011/0288529 A1 | 11/2011 | Fulton |
| 2011/0288572 A1 | 11/2011 | Martin |
| 2012/0059309 A1 | 3/2012 | Di Palma et al. |
| 2012/0083824 A1 | 4/2012 | Berrada et al. |
| 2012/0083868 A1 | 4/2012 | Shrivastava |
| 2012/0165859 A1 | 6/2012 | Eckhouse et al. |
| 2012/0271105 A1 | 10/2012 | Nakamura et al. |
| 2013/0046332 A1 | 2/2013 | Jones et al. |
| 2013/0096571 A1 | 4/2013 | Massicotte et al. |
| 2013/0116721 A1 | 5/2013 | Takagi et al. |
| 2013/0226196 A1 | 8/2013 | Smith |
| 2013/0317589 A1 | 11/2013 | Martin et al. |
| 2013/0345739 A1 | 12/2013 | Brady et al. |
| 2014/0005712 A1 | 1/2014 | Martin et al. |
| 2014/0005717 A1 | 1/2014 | Martin et al. |
| 2014/0046133 A1 | 2/2014 | Nakamura et al. |
| 2014/0155980 A1 | 6/2014 | Turjman |
| 2014/0257253 A1 | 9/2014 | Jemison |
| 2014/0276403 A1 | 9/2014 | Follmer et al. |
| 2014/0330286 A1 | 11/2014 | Wallace |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick et al. |
| 2015/0018860 A1 | 1/2015 | Quick et al. |
| 2015/0088190 A1 | 3/2015 | Jensen |
| 2015/0112376 A1 | 4/2015 | Molaei et al. |
| 2015/0164523 A1 | 6/2015 | Brady et al. |

(56) References Cited

U.S. PATENT DOCUMENTS

| | | | |
|---|---|---|---|
| 2015/0164666 A1 | 6/2015 | Johnson et al. | |
| 2015/0190155 A1 | 7/2015 | Ulm, III | |
| 2015/0190156 A1 | 7/2015 | Ulm, III | |
| 2015/0196380 A1 | 7/2015 | Berrada et al. | |
| 2015/0351775 A1 | 12/2015 | Fulton, III | |
| 2015/0359547 A1 | 12/2015 | Vale et al. | |
| 2016/0022293 A1 | 1/2016 | Dubrul et al. | |
| 2016/0058458 A1 | 3/2016 | Hansen et al. | |
| 2016/0058540 A1 | 3/2016 | Don Michael | |
| 2016/0074627 A1 | 3/2016 | Cottone | |
| 2016/0106448 A1 | 4/2016 | Brady et al. | |
| 2016/0106449 A1 | 4/2016 | Brady et al. | |
| 2016/0113663 A1 | 4/2016 | Brady et al. | |
| 2016/0113664 A1 | 4/2016 | Brady et al. | |
| 2016/0113665 A1 | 4/2016 | Brady et al. | |
| 2016/0206371 A1 | 7/2016 | Elgaard et al. | |
| 2016/0228134 A1 | 8/2016 | Martin et al. | |
| 2016/0242799 A1 | 8/2016 | Bonneau et al. | |
| 2016/0256179 A1 | 9/2016 | Walish et al. | |
| 2017/0035445 A1 | 2/2017 | Nguyen et al. | |
| 2017/0042571 A1 | 2/2017 | Levi | |
| 2017/0086864 A1 | 3/2017 | Greenhalgh et al. | |
| 2017/0100142 A1 | 4/2017 | Look et al. | |
| 2017/0105743 A1 | 4/2017 | Vale et al. | |
| 2017/0112513 A1 | 4/2017 | Marchand et al. | |
| 2017/0119411 A1 | 5/2017 | Shah | |
| 2017/0303939 A1 | 10/2017 | Greenhalgh et al. | |
| 2017/0303942 A1 | 10/2017 | Greenhalgh et al. | |
| 2017/0303947 A1 | 10/2017 | Greenhalgh et al. | |
| 2017/0303948 A1 | 10/2017 | Wallace et al. | |
| 2017/0348014 A1 | 12/2017 | Wallace et al. | |
| 2018/0042624 A1 | 2/2018 | Greenhalgh et al. | |
| 2018/0042626 A1 | 2/2018 | Greenhalgh et al. | |
| 2018/0049766 A1* | 2/2018 | Nolan | A61B 17/32056 |
| 2018/0070968 A1 | 3/2018 | Wallace et al. | |
| 2018/0236205 A1 | 8/2018 | Krautkremer et al. | |
| 2019/0046219 A1 | 2/2019 | Marchand et al. | |
| 2019/0117244 A1 | 4/2019 | Wallace et al. | |
| 2019/0133622 A1 | 5/2019 | Wallace et al. | |
| 2019/0133623 A1 | 5/2019 | Wallace et al. | |
| 2019/0133624 A1 | 5/2019 | Wallace et al. | |
| 2019/0133625 A1 | 5/2019 | Wallace et al. | |
| 2019/0133626 A1 | 5/2019 | Wallace et al. | |
| 2019/0133627 A1 | 5/2019 | Wallace et al. | |
| 2019/0336148 A1 | 11/2019 | Greenhalgh et al. | |

FOREIGN PATENT DOCUMENTS

| | | |
|---|---|---|
| CN | 102186427 | 9/2011 |
| CN | 102933161 | 2/2013 |
| CN | 102988096 | 3/2013 |
| CN | 103764049 | 4/2014 |
| CN | 103889347 | 6/2014 |
| CN | 104000635 | 8/2014 |
| CN | 104042304 | 9/2014 |
| CN | 104068910 | 10/2014 |
| CN | 104523320 | 4/2015 |
| CN | 104582608 | 4/2015 |
| CN | 108348319 | 7/2018 |
| CN | 111281482 | 6/2020 |
| EP | 1254634 | 11/2002 |
| GB | 1588072 | 4/1981 |
| GB | 2498349 | 7/2013 |
| JP | 2003-38500 | 2/2003 |
| JP | 2003-135604 | 5/2003 |
| JP | 2016-41275 | 3/2016 |
| WO | WO 00/32118 | 6/2000 |
| WO | WO 0202162 | 1/2002 |
| WO | WO 2005096963 | 10/2005 |
| WO | WO 2008/088371 | 7/2008 |
| WO | WO 2009086482 | 7/2009 |
| WO | WO 2012009675 | 1/2012 |
| WO | WO 2012049652 | 4/2012 |
| WO | WO 2012162437 | 11/2012 |
| WO | WO 2015189354 | 12/2015 |
| WO | WO 2017058280 | 4/2017 |
| WO | WO 2017189535 | 11/2017 |
| WO | WO 2017189550 | 11/2017 |
| WO | WO 2017189591 | 11/2017 |
| WO | WO 2017189615 | 11/2017 |
| WO | WO 2017210487 | 12/2017 |
| WO | WO 2018049317 | 3/2018 |
| WO | WO 2019010318 | 1/2019 |
| WO | WO 2019094456 | 5/2019 |
| WO | WO 2019222117 | 11/2019 |

OTHER PUBLICATIONS

Foreign Search Report for CN Patent Appln. No. 201780067034.4 dated Aug. 30, 2021 (with English translation).

Response to OA for EP Patent Appln. No. 19773654.9 dated Dec. 22, 2021 with Amended Claims and Description.

Extended European Search Report for EP Patent Appln. No. 21192438.6 dated Nov. 23, 2021.

Foreign Notice of Rejection for JP Patent Appln. No. 2020-093260 dated Dec. 21, 2021.

Foreign Notice of Reasons of Rejection for JP Patent Appln. No. 2019-513286 dated Jul. 26, 2021 (with English translation).

Foreign Exam Report for EP Patent Appln. No. 19773654.9 dated Aug. 24, 2021.

Foreign OA for JP Patent Appln. No. 2020-093260 dated Apr. 20, 2021.

Non-Final Office Action for U.S. Appl. No. 16/566,393 dated May 11, 2021.

Amendment Response to NFOA for U.S. Appl. No. 16/566,393 dated Aug. 11, 2021.

Non-Final Office Action for U.S. Appl. No. 16/594,259 dated Aug. 31, 2021.

Non-Final Office Action for U.S. Appl. No. 15/496,570, dated Aug. 9, 2017.

PCT International Search Report and Written Opinion for International Appln. No. PCT/US2017/029440, Applicant Stryker Corporation, dated Jul. 7, 2017.

PCT Invitation to Pay Additional Fees for International Appln. No. PCT/US2017/029366, Applicant Stryker Corporation, dated Jul. 7, 2017.

PCT International Search Report and Written Opinion for International Appln. No. PCT/US2017/029472, Applicant Stryker Corporation, dated Jul. 7, 2017.

PCT International Search Report and Written Opinion for International Appln. No. PCT/US2017/035543, Applicant Stryker Corporation, dated Aug. 14, 2017.

PCT International Search Report and Written Opinion for International Appln. No. PCT/US2017/029366, Applicant Stryker Corporation, dated Aug. 29, 2017.

PCT Invitation to Pay Additional Fees for International Appln. No. PCT/US2017/029345, Applicant Stryker Corporation, dated Oct. 17, 2017.

Non-Final Office Action for U.S. Appl. No. 15/496,786, dated Nov. 1, 2017.

PCT International Search Report and Written Opinion for International Appln. No. PCT/US2017/050933, Applicant Stryker Corporation, forms PCT/ISA/210, 220, and 237, dated Nov. 10, 2017 (16 pages).

Response to Non-Final Office Action for U.S. Appl. No. 14/496,786, filed Feb. 1, 2018.

Non-final office action dated Feb. 1, 2018 for U.S. Appl. No. 15/496,668.

Response to Restriction for U.S. Appl. No. 15/496,668, filed Feb. 21, 2018.

International search report and written opinion dated Feb. 28, 2018 for PCT/US2017/029345, Applicant Stryker Corporation 26 pages.

Notice of Allowance dated Mar. 22, 2018 for U.S. Appl. No. 15/496,668.

Notice of Allowance dated Apr. 19, 2018 for U.S. Appl. No. 15/496,570.

Notice of Allowance dated Apr. 19, 2018 for U.S. Appl. No. 15/496,786.

(56) References Cited

OTHER PUBLICATIONS

Non-Final Office Action dated Sep. 5, 2018 for U.S. Appl. No. 15/291,015.
Extended European Search Report dated Aug. 22, 2018 for European patent appln No. 16852212.6.
Extended European Search Report dated Oct. 5, 2018 for European patent appln No. 18174891.4.
Invitation to Pay Additional Fees for International Patent Appln. No. PCT/US2018/040937 dated Sep. 26, 2018.
Response to Non-Final Office Action for U.S. Appl. No. 15/291,015, filed Sep. 5, 2018.
International search report and written opinion dated Nov. 14, 2018 for PCT/US2018/040937, Applicant Stryker Corporation 16 pages.
Notice of Allowance dated Dec. 11, 2018 for U.S. Appl. No. 15/291,015.
Invitation to Pay Additional Fees for International Patent Appln. No. PCT/US2018/059607 dated Jan. 31, 2019.
Japanese Office action mailed Mar. 19, 2019 for Japanese Application No. 2018-535810 (with English Language translation).
International Search Report and Written Opinion dated Mar. 28, 2019 for International Appln. No. PCT/US2018/059607.
Notice of Allowance dated Apr. 10, 2019 for U.S. Appl. No. 15/611,546.
Response to Extended European Search Report for EP Patent Appln. No. 16852212.6 dated Mar. 15, 2019.
European Patent Office Communication Rule 161 (1) and 162 dated Feb. 5, 2019 for EP Patent Appln. No. 17729703.3.
European Patent Office Communication Rule 161(1) and 162 EPC for EP Patent Appln. No. 17737084.8 dated Dec. 18, 2018.
European Patent Office Communication Rule 161(1) and 162 for EP Patent Appln. No. 17722277.5 dated Dec. 13, 2018.
European Patent Office Communication Rule 161(1) and 162 dated Dec. 13, 2018 for EP Patent Appln. No. 17722290.8.
European Patent Office Communication Rule 161(1) and 162 dated Dec. 13, 2018 for EP Patent Appln. No. 17721036.6.
Response to Extended European Search Report for EP Patent Appln. No. 18174891.4 dated May 28, 2019.
Restriction Requirement dated Jun. 28, 2019 for U.S. Appl. No. 15/700,685.
International Search Report and Written Opinion dated May 6, 2016 for PCT/US2016/017982.
Response to European Patent Office Communication Rule 161 (1) and 162 EPC filed Jun. 11, 2019, for EP Patent Appln. No. 17737084.8.
Response to European Patent Office Communication Rule 161(1) and 162 filed Jun. 4, 2019 for EP Patent Appln. No. 17722277.5.
Response to European Patent Office Communication Rule161(1) and 162 filed Jun. 4, 2019 for EP Patent Appln. No. 17722290.8.
Response to European Patent Office Communication 161(1) and 162 filed Jun. 11, 2019 for EP Patent Appln. No. 17721036.6.
European Patent Office Communication Rule161(1) and 162 dated Apr. 23, 2019 for EP Patent Appln. No. 17772186.7.
Response to Non-Final Office Action filed Nov. 8, 2017 for U.S. Appl. No. 15/496,570.
Response to Non-Final Office Action filed Feb. 1, 2018 for U.S. Appl. No. 15/496,786.
Restriction Requirement dated Apr. 11, 2019 for U.S. Appl. No. 15/497,092.
Response to Restriction Requirement filed Jun. 11, 2019 for U.S. Appl. No. 15/497,092.
Ex Parte Quayle office action dated Jul. 16, 2019 for U.S. Appl. No. 15/497,092.
Response to Rule 161(1) and 162 EPC filed on Jul. 23, 2019 for EP application No. 17729703.3.
PCT International Search Report and Written Opinion for International Patent Appln. No. PCT/US2019/032601, Applicant Stryker Corporation, dated Jul. 23, 2019 (12 pages).
Response to Restriction Requirement filed Jul. 25, 2019 for U.S. Appl. No. 15/700,685.
Response to Ex Parte Quayle office action filed Jul. 25, 2019 for U.S. Appl. No. 15/497,092.
Office action dated Jun. 5, 2019 for Chinese application No. 2019053101871820, including partial English language translation provided by the foreign associate.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html; 5 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 2 pgs .; retrieved/printed: Mar. 24, 2016.
Youtube; Merci Retrieval System X Series Animation; uploaded Mar. 16, 2009 (product information); retrieved from the internet: https://www.youtube.com/watch?v=MGX7deuFkhc; 3 pgs.; retrieved/printed: Mar. 24, 2016.
COVIDIEN; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.
Notice of Allowance for U.S. Appl. No. 15/043,996 dated Jun. 9, 2016.
Ex Parte Quayle office action dated Aug. 2, 2019 for U.S. Appl. No. 15/497,092.
Non Final Office Action dated Aug. 23, 2019 for U.S. Appl. No. 15/700,685.
Non Final Office Action dated Sep. 3, 2019 for U.S. Appl. No. 15/794,939.
Rule 71(3) Allowance for EP Patent Appln. No. 18174891.4 dated Jul. 30, 2019.
Response to Ex Parte Quayle office action filed Sep. 17, 2019 for U.S. Appl. No. 15/497,092.
Office action response filed on Sep. 26, 2019 for Chinese Patent Application No. 2016800567527, no translation received.
Non-Final Office Action dated Oct. 4, 2019 for U.S. Appl. No. 15/795,097.
Response to Restriction filed Oct. 4, 2019 for U.S. Appl. No. 15/795,097.
Notice of Allowance dated Sep. 27, 2019 for U.S. Appl. No. 15/497,092.
Extended European Search Report dated Oct. 8, 2019 for European Patent Application No. 19191925.7.
Office action dated Oct. 7, 2019 for European Patent Application No. 17729703.3.
Office action dated Oct. 7, 2019 for European Patent Application No. 17737084.8.
Response to European Patent Office Communication Rule161(1) and 162 filed Oct. 17, 2019 for EP Patent Appln. No. 17772186.7.
Invitation to Pay Additional Fees for International Patent Appln. No. PCT/US2019/050467 dated Oct. 25, 2019.
International Search Report and Written Opinion for International Patent Appln. No. PCT/US2019/050410 dated Oct. 25, 2019.
Notice of Allowance dated Oct. 24, 2019 for U.S. Appl. No. 15/611,546.
Response to Non Final Office Action filed Nov. 8, 2019 for U.S. Appl. No. 15/700,685.
Notice of Allowance dated Nov. 6, 2019 for U.S. Appl. No. 15/795,097.

(56) References Cited

OTHER PUBLICATIONS

Rule 71(3) Allowance for EP Patent Appln. No. 17721036.6 dated Oct. 23, 2019.
Rule 71(3) Allowance for EP Patent Appln. No. 17722290.8 dated Nov. 11, 2019.
Notice of Allowance dated Nov. 21, 2019 for U.S. Appl. No. 15/700,685.
Amendment Response dated Dec. 3, 2019 for U.S. Appl. No. 15/794,939.
PCT International Search Report and Written Opinion for International Patent Appln. No. PCT/US2019/050467, Applicant Stryker Corporation, dated Dec. 18, 2019 (17 pages).
Non Final Office Action dated Dec. 27, 2019 for U.S. Appl. No. 16/594,256.
Final Office Action dated Mar. 2, 2020 for U.S. Appl. No. 15/794,939.
Notice of Allowance for U.S. Appl. No. 15/794,939 dated Mar. 31, 2020.
Amendment Response dated Mar. 27, 2020 for U.S. Appl. No. 16/594,256.
Non-Final Office Action for U.S. Appl. No. 16/096,031 dated May 8, 2020.
Non-Final Office Action for U.S. Appl. No. 16/183,162 dated May 13, 2020.
Non-Final Office Action for U.S. Appl. No. 16/169,334 dated May 8, 2020.
Non-Final Office Action for U.S. Appl. No. 16/183,171 dated May 13, 2020.
Foreign OA for Japanese Patent Application No. 2018-535810 dated Feb. 7, 2020.
Amendment Response to Non-Final Office Action for U.S. Appl. No. 16/183,171 dated Jul. 30, 2020.
Amendment Response to Non-Final Office Action for U.S. Appl. No. 16/183,162 dated Jul. 30, 2020.
Applicant Interview Summary for U.S. Appl. No. 16/096,031 dated Jul. 30, 2020.
Applicant Interview Summary for U.S. Appl. No. 16/169,334 dated Jul. 30, 2020.
Applicant Interview Summary for U.S. Appl. No. 16/183,133 dated Aug. 24, 2020.
Non-Final Office Action for U.S. Appl. No. 16/183,149 dated Aug. 18, 2020.
Extended European Search Report for EP Patent Appln. No. 20185092.2 dated Sep. 11, 2020.
EP Examination Report for EP Patent Appln. No. 18745794.0 dated Jul. 20, 2020.
Amendment Response to NFOA for U.S. Appl. No. 16/183,149 dated Sep. 25, 2020.
Notice of Allowance for U.S. Appln. No. 16/183, 149, dated Oct. 9, 2020.
Foreign OA for CN Patent Appln. No. 2017800393642, dated Dec. 1, 2020.
Foreign OA for CN Patent Appln. No. 2017800393676, dated Dec. 2, 2020.
Foreign OA for CN Patent Appln. No. 2017800396566, dated Dec. 3, 2020.
Foreign OA for CN Patent Appln. No. 2017800343357, dated Jan. 6, 2021.
Applicant's Response filed in EP Patent Appln. No. 18807524.6, dated Dec. 21, 2020.
PCT International Search Report and Written Opinion for International Appln. No. PCT/US2020/014854, dated Oct. 5, 2020 (13 pages).
PCT International Search Report and Written Opinion for International Appln. No. PCT/US2020/018655, dated Dec. 16, 2020 (22 pages).
PCT International Search Report and Written Opinion for International Appln. No. PCT/US2020/017684, dated Nov. 30, 2020 (19 pages).
Foreign OA for JP Patent Appln. No. 2019-507078 dated Feb. 3, 2021.
Foreign OA for JP Patent Appln. No. 2019-507075 dated Feb. 1, 2021.
Notice of Allowance for U.S. Appl. No. 16/397,089 dated Feb. 18, 2021.
Foreign OA for JP Patent Appln. No. 2018-562633 dated Mar. 4, 2021.
Foreign Communication Under Rule 71(3) for EP Patent Appln. No. 18807524.6 dated Jul. 1, 2022.
Foreign Communication Pursuant to Article 94(3) for EP Patent Appln. No. 17772186.7 dated Jun. 17, 2022.
Foreign OA for JP Patent Appln. No. 2019-513286 dated May 10, 2022.
Foreign OA for JP Patent Appln. No. 2019-571360 dated Jun. 9, 2022.
Amendment Response to NFOA for U.S. Appl. No. 16/707,045 dated Jul. 11, 2022.
Extended European Search Report for EP Patent Appln. No. 22162955.3 dated Sep. 5, 2022.
Foreign Notice of Rejection for JP Patent Appln. No. 2020-093260 dated Aug. 2, 2022.
Final Office Action for U.S. Appl. No. 16/707,045 dated Jul. 22, 2022.
Foreign Response for EP Patent Appln. No. 21192438.6 dated Jul. 18, 2022.
Foreign Response for JP Patent Appln. No. 2021-72088 dated Jul. 4, 2022.
Notice of Rejection for JP Patent Appln. No. 2020-523723 dated Aug. 8, 2022 with English translation.
Notice of Allowance for U.S. Appl. No. 16/790,744 dated Jun. 17, 2022.
Notice of Allowance for U.S. Appl. No. 16/731,649 dated Jul. 20, 2022.
Foreign OA for CN Patent Appln. No. 201880046302.9 dated Aug. 25, 2022 (with English translation).
Foreign OA for JP Patent Appln. No. 2021-125123 dated Aug. 23, 2022.
Non-Final Office Action for U.S. Appl. No. 16/707,045 dated Nov. 14, 2022.
Non-Final Office Action for U.S. Appl. No. 16/594,259 dated Nov. 9, 2022.
Notice of Allowance for U.S. Appl. No. 16/722,880 dated Oct. 5, 2022.
Non-Final Office Action for U.S. Appl. No. 16/790,741 dated Nov. 1, 2022.
Foreign OA for CN Patent Appln. No. 202010148570.0 dated Nov. 1, 2022.
Foreign Search Report for CN Patent Appln. No. 202010148570.0 dated Nov. 1, 2022.
Foreign Response for EP Patent Appln. No. 21211363.3 dated Mar. 17, 2022.
Foreign Exam Report for IN Patent Appln. No. 202147016629 dated Mar. 2, 2022.
Foreign OA for IN Patent Appln. No. 202147016649 dated Mar. 28, 2022.
Non-Final Office Action for U.S. Appl. No. 16/707,045 dated Apr. 11, 2022.
Foreign OA for CN Patent Appln. No. 2017800670344 dated Mar. 21, 2022 with English Translation.
Foreign OA for JP Patent Appln. No. 2021-072088 dated Apr. 5, 2022 with English translation.
Foreign OA for EP Patent Appln. No. 19726855.0 dated May 18, 2022.
Amendment Response to NFOA for U.S. Appl. No. 17/169,334 dated Apr. 3, 2023.
Foreign OA for JP Patent Appln. No. 2020-564233 dated Jan. 31, 2023 (with English translation).
Amendment Response to NFOA for U.S. Appl. No. 16/790,741 dated Nov. 21, 2022.
Amendment Response to NFOA for U.S. Appl. No. 16/594,259 dated Jan. 26, 2023.
Notice of Allowance for U.S. Appl. No. 16/790,741 dated Dec. 21, 2022.

(56) References Cited

OTHER PUBLICATIONS

Non-Final Office Action for U.S. Appl. No. 16/169,334 dated Jan. 6, 2023.
Foreign OA for CN Patent Appln. No. 201880072826.5 dated Oct. 12, 2022 (with English translation).
Foreign Search Report for CN Patent Appln. No. 201880072826.5 dated Oct. 12, 2022 (with English translation).
Final Office Action for U.S. Appl. No. 16/594,259 dated Mar. 1, 2023.

* cited by examiner

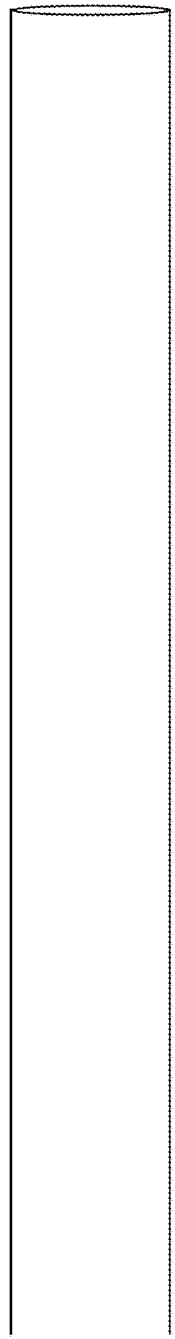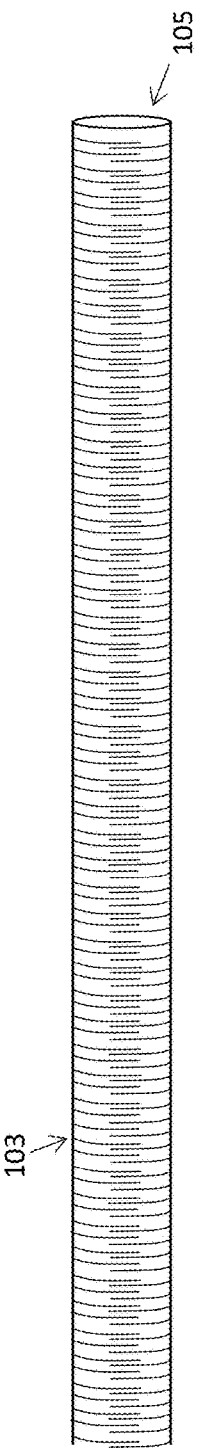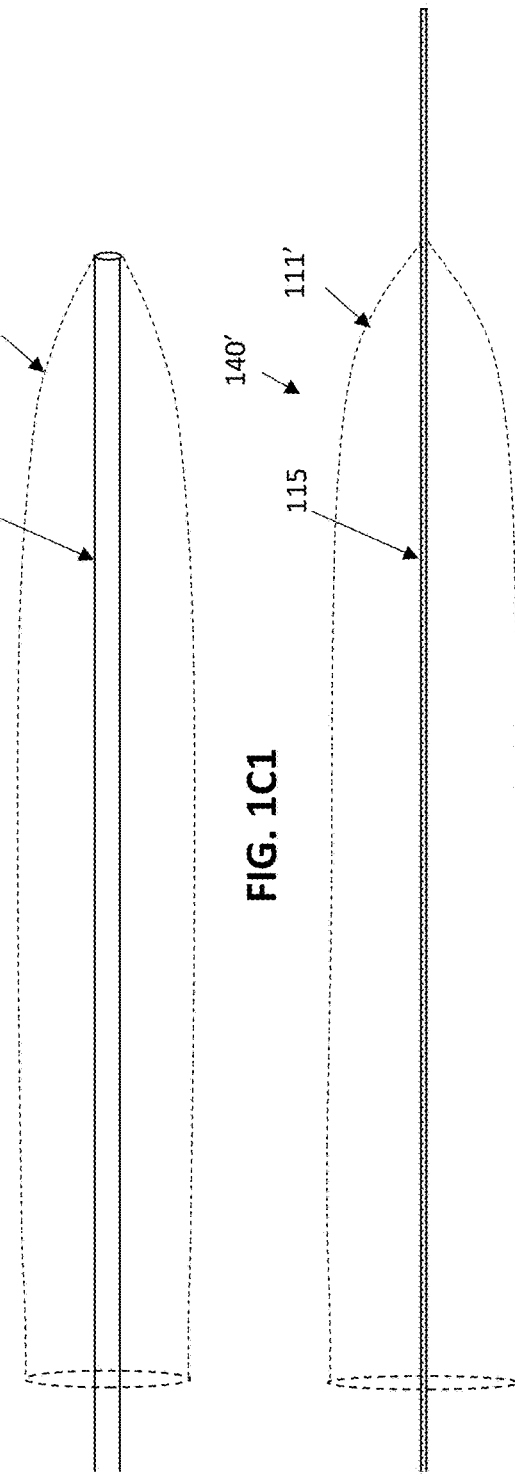

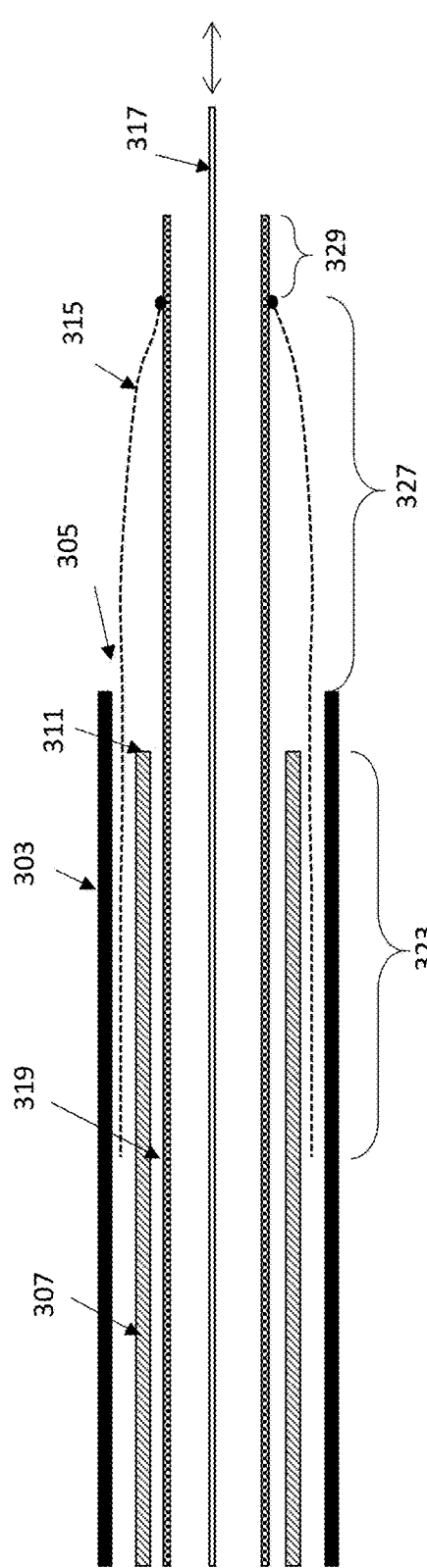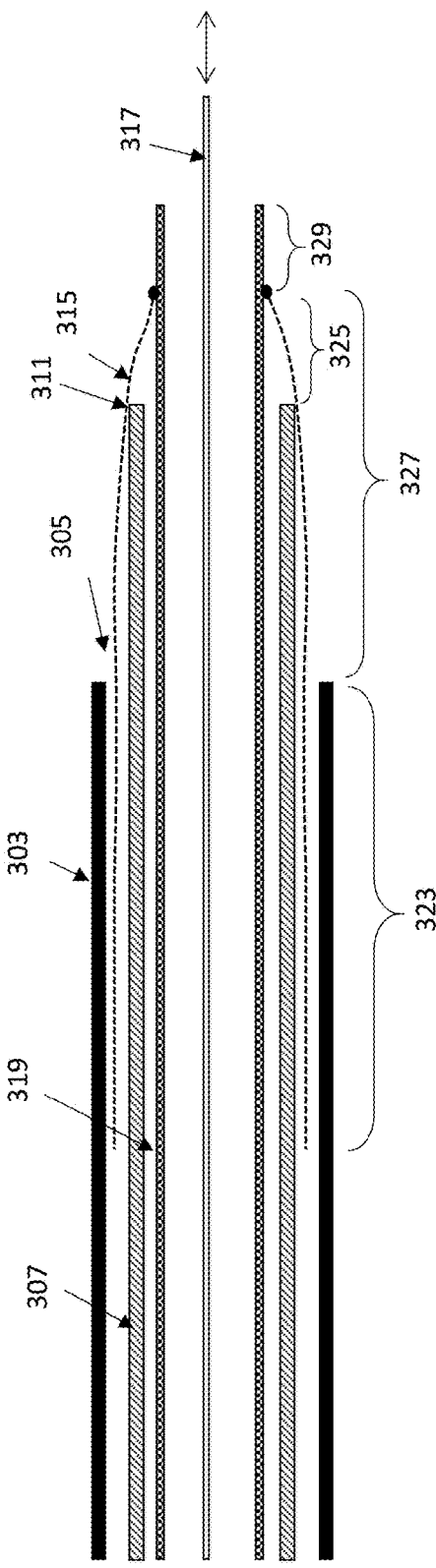
FIG. 3A
FIG. 3B

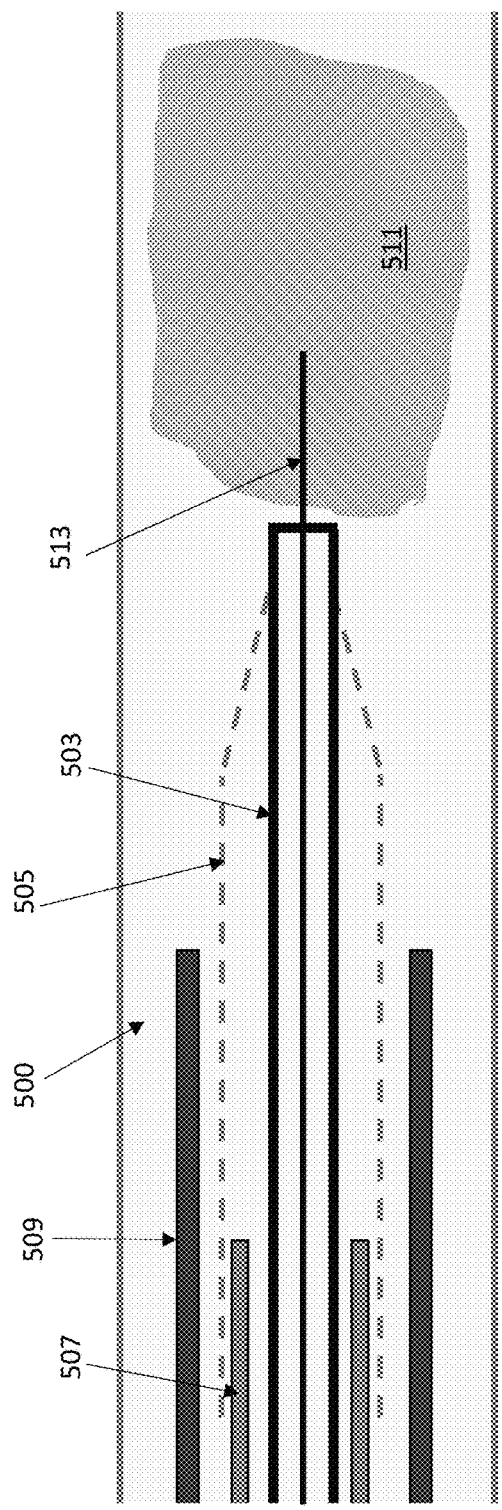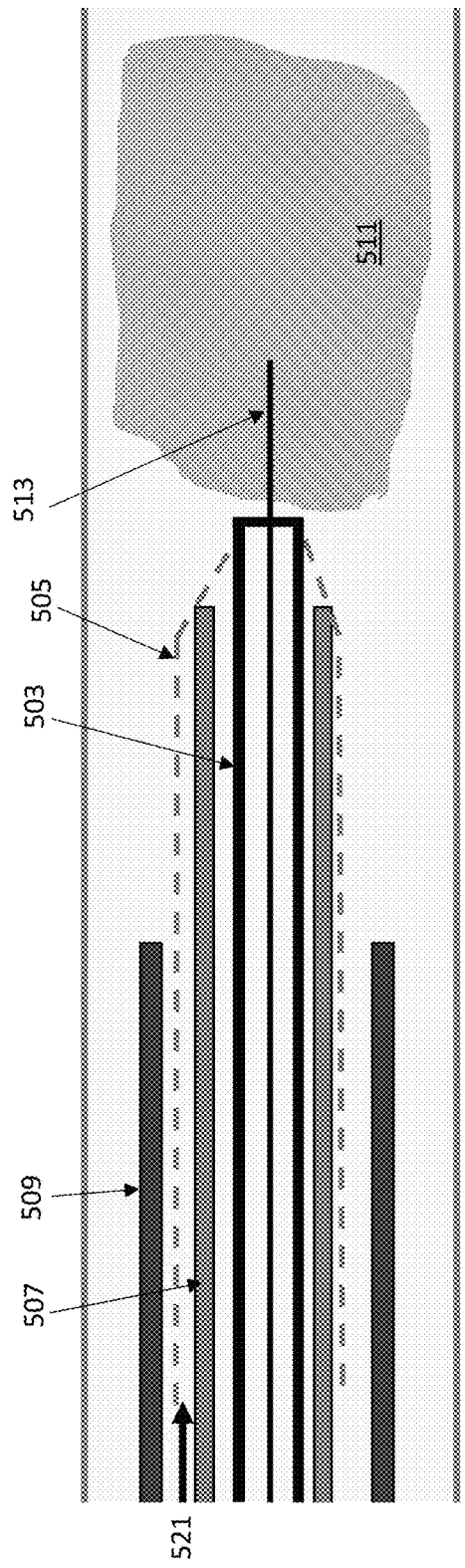
FIG. 5A
FIG. 5B

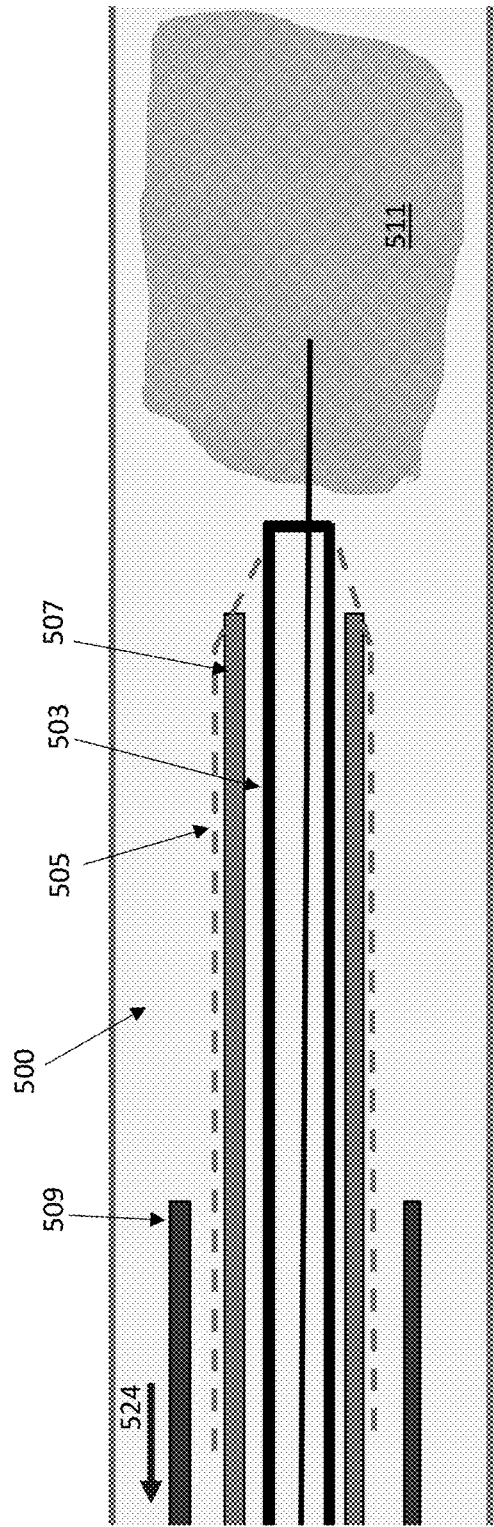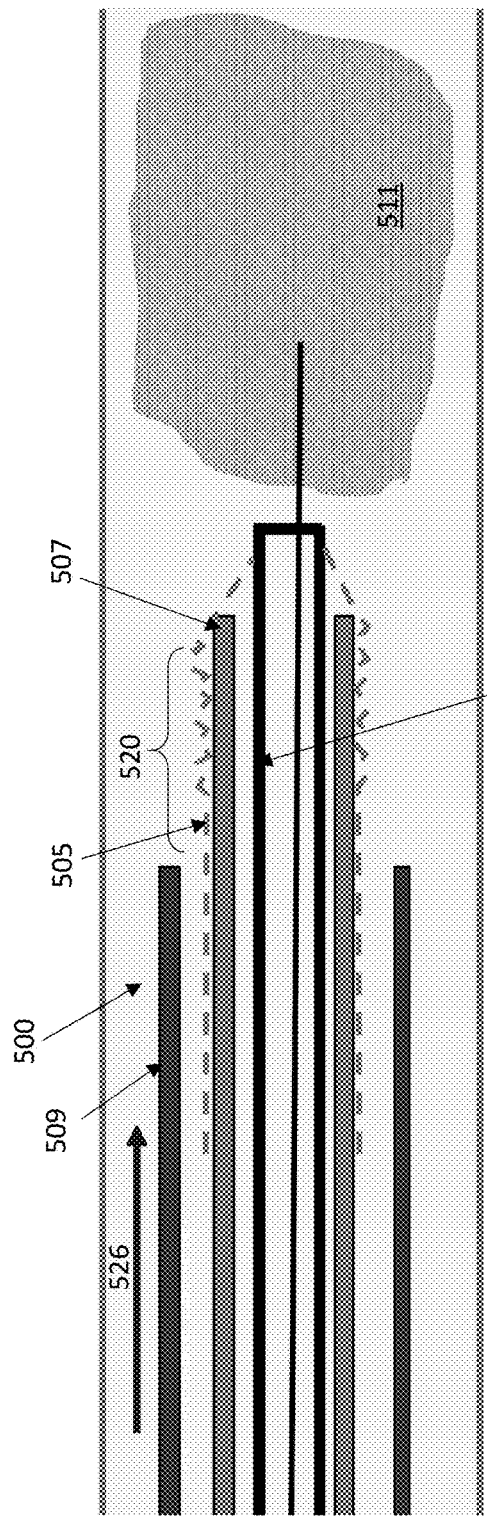

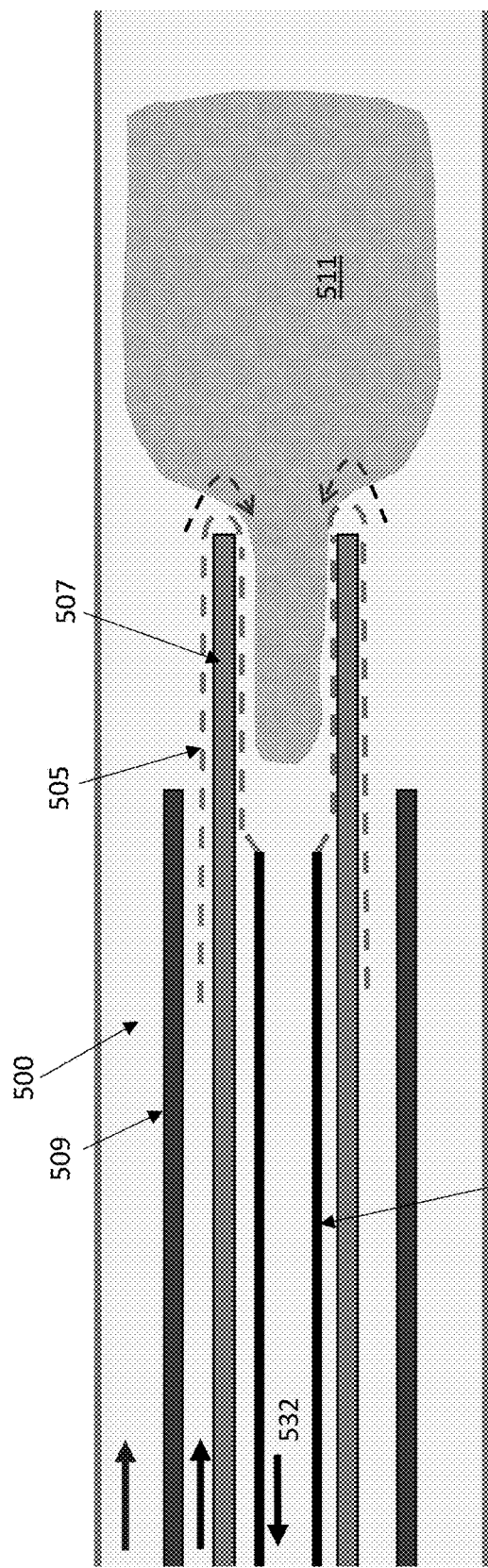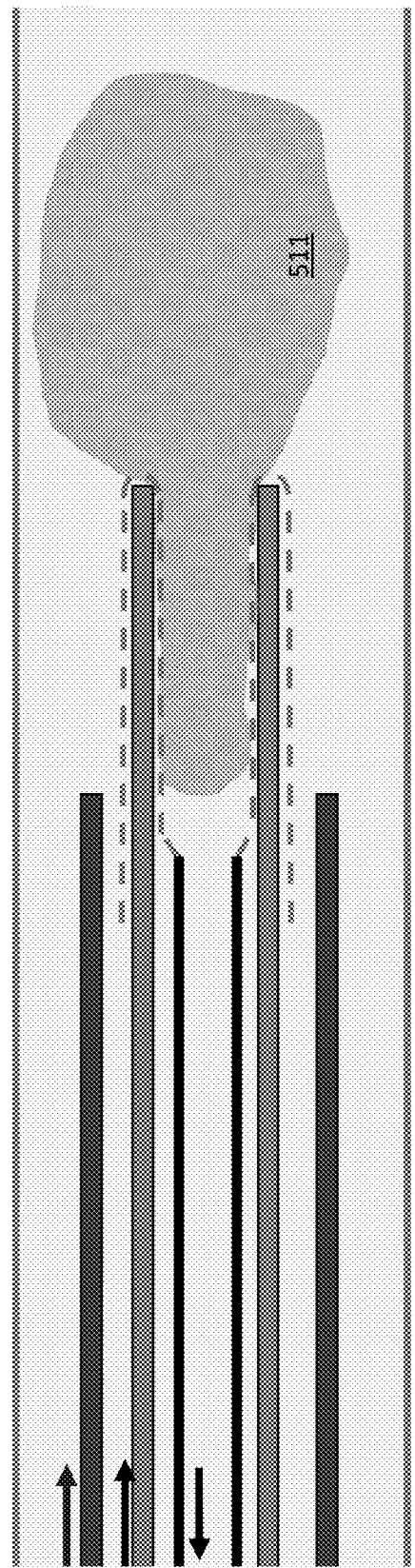

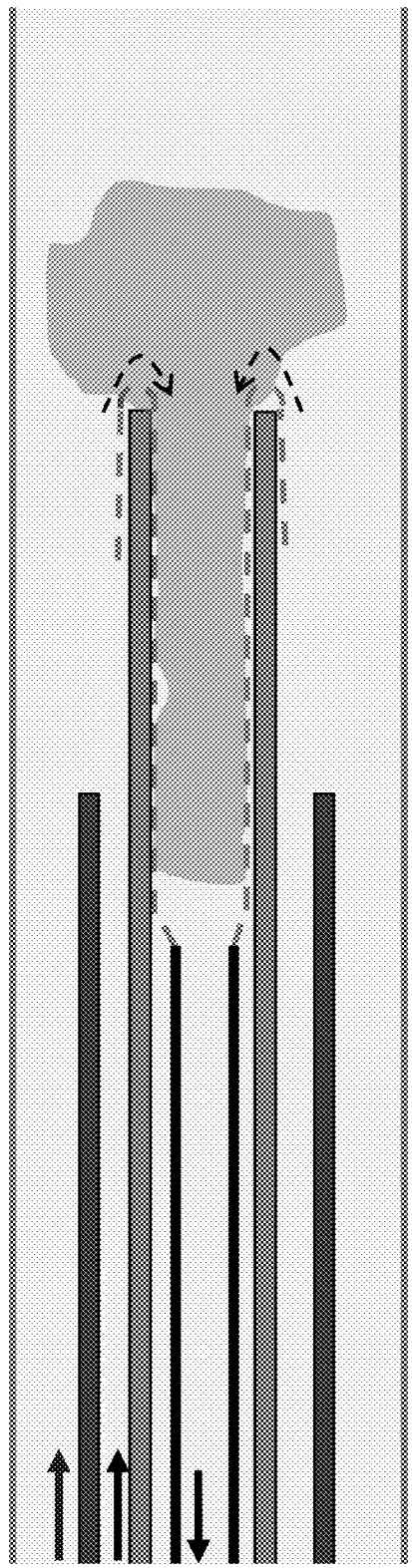
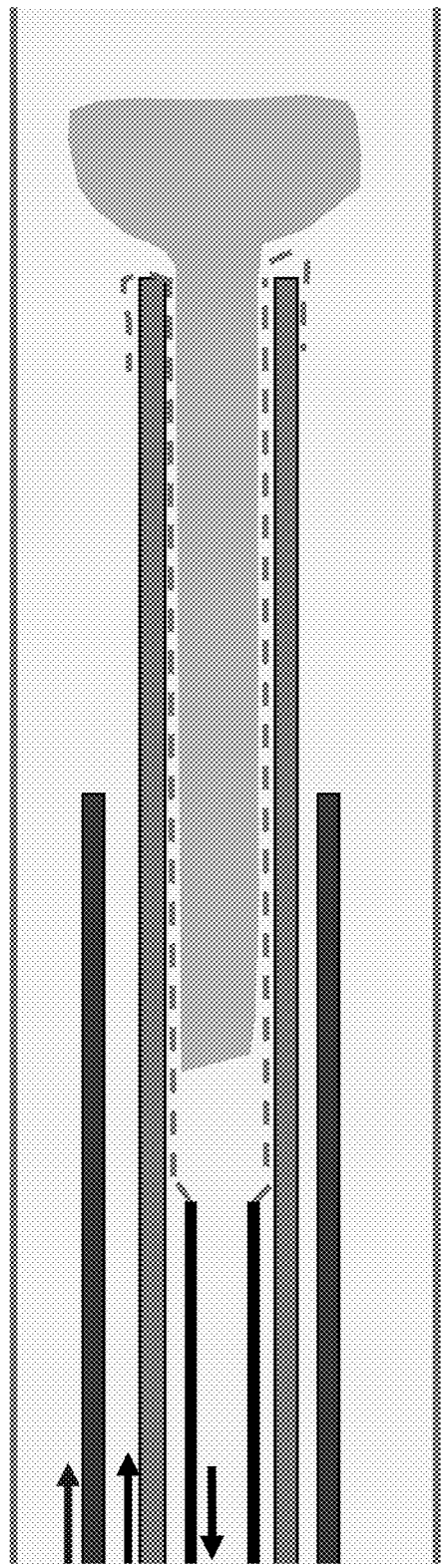
FIG. 5I
FIG. 5J

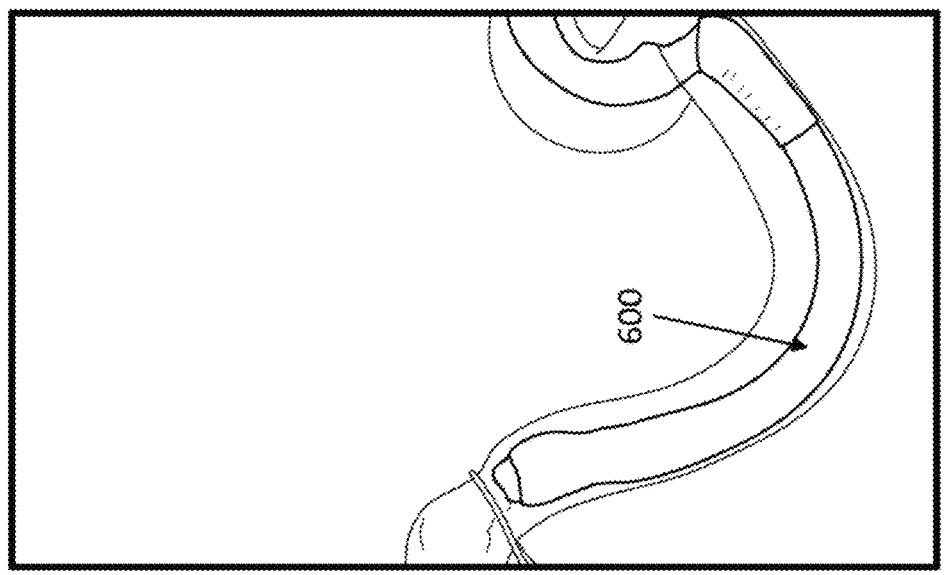
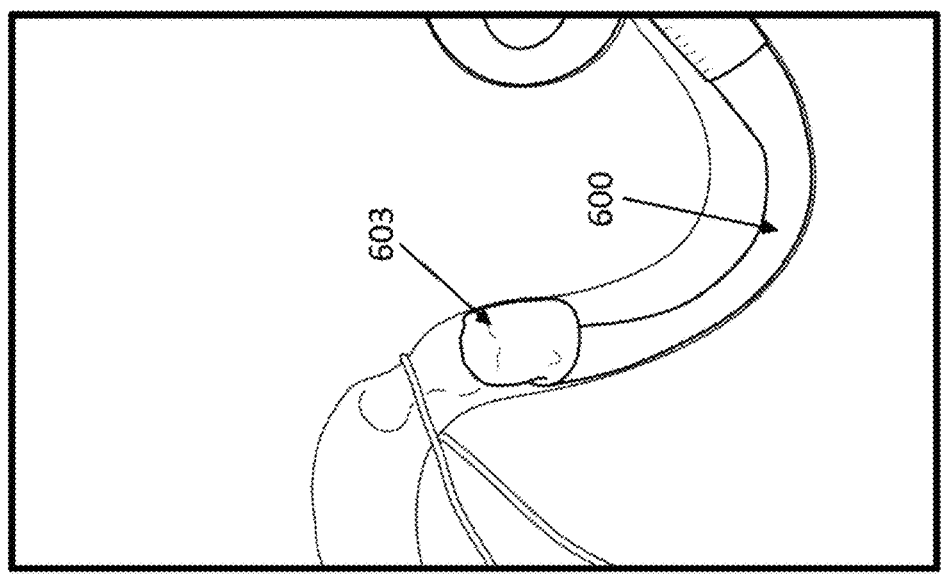
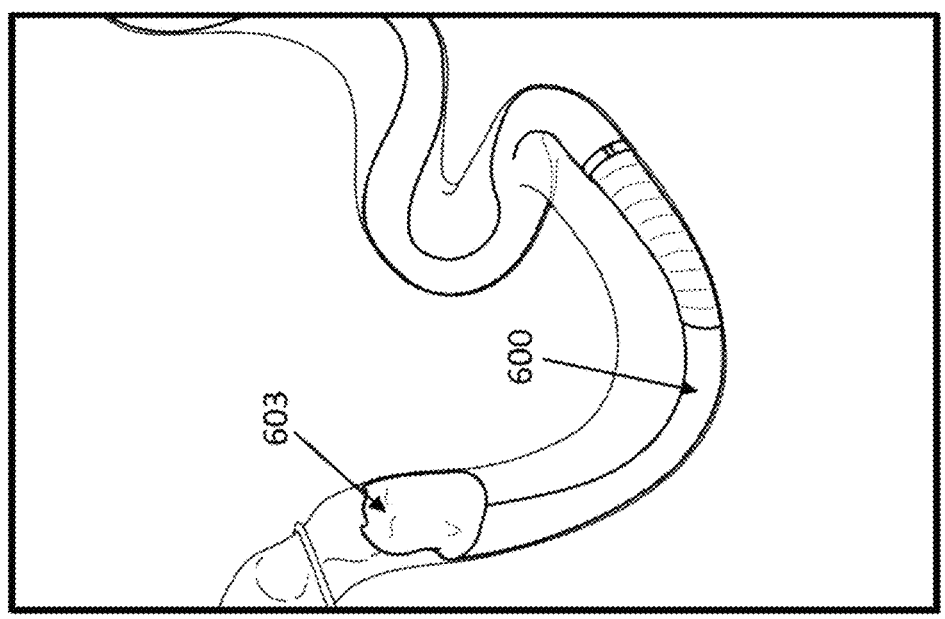

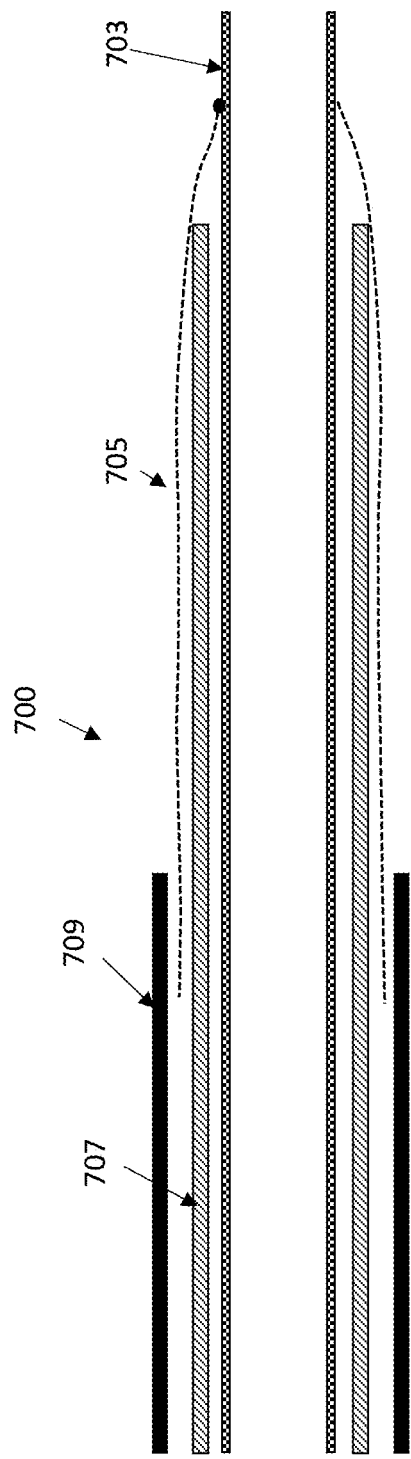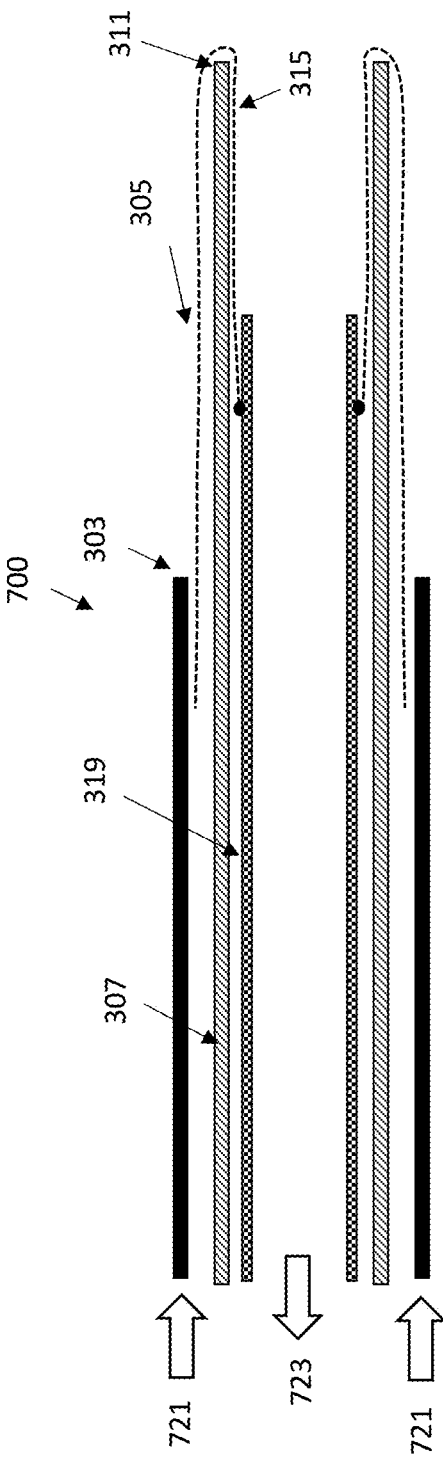

(not to scale)

INVERTING THROMBECTOMY APPARATUSES AND METHODS OF USE

CROSS REFERENCE TO RELATED APPLICATIONS

This patent application is a continuation of U.S. patent application Ser. No. 16/410,946, filed on May 13, 2019, which claims priority to U.S. provisional patent application Ser. No. 62/671,143 ("INVERTING THROMBECTOMY APPARATUSES AND METHODS OF USE") filed on May 14, 2018.

This application may be related to one or more of: U.S. application Ser. No. 15/291,015, filed on Oct. 11, 2016 ("Mechanical Thrombectomy Apparatuses and Methods"); U.S. application Ser. No. 15/496,570, filed on Apr. 25, 2017 ("Anti-Jamming and Macerating Thrombectomy Apparatuses and Methods"), U.S. application Ser. No. 15/496,668, field on Apr. 25, 2017 ("Pre-loaded Inverting Tractor Thrombectomy Apparatuses and Methods"); U.S. application Ser. No. 15/496,786, filed on Apr. 25, 2017 ("Methods for Advancing Inverting Mechanical Thrombectomy Apparatuses in the Vasculature"); U.S. application Ser. No. 15/497,092, filed on Apr. 25, 2017 ("Clot-Engulfing Mechanical Thrombectomy Apparatuses and Methods of Use"); and U.S. application Ser. No. 15/611,546, filed on Jun. 1, 2017 ("Inverting Thrombectomy Apparatuses and Methods").

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate to mechanical removal of objects from within a body. In particular, described herein are mechanical thrombectomy apparatuses and methods.

BACKGROUND

Many vascular problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery. It is often desirable to remove tissue from the body in a minimally invasive manner as possible, so as not to damage other tissues. For example, removal of tissue, such as blood clots, from within a patient's vasculature may improve patient conditions and quality of life.

Mechanical thrombectomy devices may be particularly advantageous. There is a definite need for thrombectomy devices, and particularly a mechanical thrombectomy devices that can be easily and accurately delivered through the often tortious anatomy in the peripheral and central vasculature, then reliably deployed to remove clot material. Further, there is a need for devices that are easy and intuitive to operate. Described herein are apparatuses (devices, systems and kit) and methods of using them that may address the needs and problems discussed above.

SUMMARY OF THE DISCLOSURE

Described herein are mechanical thrombectomy apparatuses (devices, systems, etc.) and methods of using and making them. These apparatuses may also be referred to as inverting mechanical thrombectomy apparatuses and/or inverting tube thrombectomy apparatuses.

In particular, described herein are inverting tube thrombectomy apparatuses that may be deployed within even the most tortious vessels of the anatomy and may maintain their proximity to the clot during operation. Generally, the inverting tube thrombectomy apparatuses described herein may include an inner puller (which may be configured as a puller catheter), an inverting flexible tube attached at a distal end region of the puller, and an outer inversion support catheter; the flexible tube may initially extend over an external region at the distal end of the inversion support catheter. All or a portion of the inversion support catheter, flexible tube and puller may be housed within an intermediate (e.g., delivery) catheter. In operation, the puller may be pulled to roll and invert the flexible tube over the open distal end of the inversion support catheter. This rolling and inversion of the flexible tube may capture a material, such as a clot, and pull it into the inner lumen of the inversion support catheter as the flexible tube is rolled and inverted.

Specifically, the inverting tube thrombectomy apparatuses and methods of operating them may prevent or reduce compression of the distal end of the inversion support catheter that may otherwise separate the end of the apparatus from the clot (e.g., kick back) and make further tracking of the apparatus within a tortious vessel difficult. Thus, in some variations of inverting tube thrombectomy apparatuses, pulling on the inverting tube (e.g., woven/braided/etc. tractor) compresses the distal end of the inversion support catheter (particularly in tortious anatomy), and causes it to separate from the clot and make additional tracking difficult within the tortious vessel.

Thus, any of the apparatuses described herein may be configured to prevent tension in the external portion of the flexible tube that is on the outer surface of the inversion support catheter before and/or during rolling and inverting the flexible tube over the distal end of the inversion support catheter.

Also described herein are methods for removing a clot (or multiple portions of a clot, or multiple clots) from a vessel. For example, a method of removing a clot from a vessel may include: advancing an inverting tube thrombectomy apparatus through a vessel until a distal end of the inverting tube thrombectomy apparatus is proximate to the clot, wherein the inverting tube thrombectomy apparatus comprises an inversion support catheter, a puller catheter slideable within a lumen of the inversion support catheter, and a flexible tube having a first end coupled at a distal end region of the puller catheter and a second end coupled to the inversion support catheter; applying aspiration through a lumen in the puller catheter to hold the clot on a distal end of the puller catheter; pushing the inversion support catheter distally to form slack in the flexible tube; and pulling the puller catheter proximally relative to the inversion support catheter to roll and invert the inversion support catheter over the distal end of the inversion support catheter and pull the clot into the inversion support catheter. This process may be repeated multiple times without removing the apparatus from the vessel.

For example, described herein are methods of removing a clot from a vessel, the method comprising: advancing an inverting tube thrombectomy apparatus through a vessel until a distal end of the inverting tube thrombectomy apparatus is proximate to the clot, wherein the inverting tube thrombectomy apparatus comprises an inversion support catheter, a puller catheter slideable within a lumen of the inversion support catheter, and a flexible tube having a first end coupled at a distal end region of the puller catheter and a second end coupled to the inversion support catheter; applying aspiration through a lumen of the puller catheter to hold the clot on a distal end of the puller catheter; pushing the inversion support catheter distally to expand the flexible tube radially outward; pulling the puller catheter proximally while advancing the inversion support catheter distally to roll and invert the inversion support catheter over the distal end of the inversion support catheter and pull the clot into the inversion support catheter; and pulling the clot proximally though the lumen of the puller catheter.

Thus, pushing the inversion support catheter distally to form slack in the flexible tube may include expanding the flexible tube radially outward from the puller catheter.

Any of these methods may include pulling the clot proximally though the lumen of the puller catheter. For example, pulling the clot proximally through the lumen of the puller catheter may comprise aspirating the clot through the puller catheter, and/or using a wire to draw the clot proximally through the lumen of the puller catheter.

Any of these methods may include reloading the inverting tube thrombectomy apparatus while still in the vessel so that additional clot may be removed with the same device. Thus, any of these methods may include removing a second clot with the inverting tube thrombectomy apparatus. Reloading the inverting tube thrombectomy apparatus may comprise advancing the puller catheter distally relative to the inversion support catheter. Reloading may be done automatically or manually. For example, advancing the puller catheter distally may releasing the puller catheter so that a bias advances the puller catheter distally (e.g., automatically or semi-automatically).

In any of these methods, pulling the puller catheter proximally may comprise applying vacuum through the lumen of the puller catheter. Vacuum may be applied through the entire procedure (e.g., continuously) or through just a portion of the procedure, e.g., when drawing the clot proximally through the lumen of the puller catheter.

Any of these methods may include the use of an inverting tube thrombectomy apparatus that includes an intermediate catheter; the inversion support catheter and the puller catheter may be held (slidably held) within the intermediate catheter for delivery and may be extended from the intermediate catheter when the distal end is near the clot.

For example, in some variations, the apparatus and/or method of using it may be configured to form slack in an external portion of the flexible tube on the outer surface of the inversion support catheter. Slack may be formed by driving the second end of the flexible tube (that may not be attached to anything, including the intermediate catheter or the inversion support catheter) distally over the inversion support catheter. In some variations the second end of the flexible tube may be held between the inversion support catheter outer surface and the intermediate catheter. For example, in an un-deployed state, the inverting tube thrombectomy apparatus may be tracked through the vasculature with most of the flexible tube, inversion support catheter and puller housed within the intermediate catheter. This assembly may be tracked through the vasculature over a guidewire, for example, in some variations, the puller and the attached first end of the flexible tube may be extended slightly out of the distal end of the intermediate catheter. Once deployed at the clot, the intermediate catheter may be withdrawn proximally (or the pusher, flexible tube and/or inversion support catheter extended distally out of the intermediate catheter) but leaving a portion of the second end of the flexible tractor between the intermediate catheter and the inversion support catheter; advancing the intermediate catheter distally may then bunch up (form slack) the flexible tube. The pusher may be held fixed, advanced distally or (in the variation described below, pulled proximally). Alternatively, in some variations the intermediate catheter may be fully removed from over the flexible tube and advancing it distally may push on the end of the flexible tube (which may include a cuff), to drive the flexible tube distally. The second end of the flexible tube may be adapted so that it may be pushed by the intermediate catheter. As mentioned, the second end of the flexible tube may include a cuff, which may be a region of relative stiffness compared to the adjacent region of the flexible tube.

In some variations, apparatus and method are configured to both push on the second end of the flexible tube distally, and pull on the first end by pulling the puller (e.g., puller catheter) proximally. This may limit or reduce tension on the outside portion of the tractor. Thus, in any of these methods, the intermediate catheter may be pushed distally at the same time the puller is pulled proximally (at the same, or different rates) to reduce tension on the outside portion of the flexible tube, thereby reducing the compressive force applied to the distal end of the inversion support catheter.

For example, described herein are method of removing a clot from a vessel that may include: advancing an inverting tube thrombectomy apparatus through a vessel until a distal end of the inverting tube thrombectomy apparatus is proximate to the clot, wherein the inverting tube thrombectomy apparatus comprises an intermediate catheter, an inversion support catheter within a lumen of the intermediate catheter, a puller within a lumen of the inversion support catheter, and a flexible tube having a first end coupled at a distal end region of the puller, wherein flexible tube inverts over a distal end of the inversion support catheter and an external portion of the flexible tube extends proximally over the inversion support catheter; positioning the puller and inversion support catheter adjacent to the clot; and pushing a proximal end region of the external portion of the flexible tube distally over the inversion support catheter during one or both of: before or while pulling the puller proximally so that the external portion of the flexible tube rolls and inverts over the distal end of the inversion support catheter.

Pushing the proximal end region of the external portion of the flexible tube may include pushing the proximal end region of the external portion of the flexible tube by advancing the intermediate catheter distally. Alternatively or additionally, the proximal end region of the external portion of the flexible tube (which may be referred to as the second end of the flexible tube) may be pushed by a different member, such as a push wire or rod.

In some variations, pushing the proximal end region of the external portion of the flexible tube comprises pushing the proximal end region of the external portion of the flexible tube before pulling the puller proximally to form slack in the external portion of the flexible tube. Slack may refer to a region in which the flexible tube is not under tension, and may be loose; in some variations the slack region may be bunched up on itself. In some variations the slack region may be compressed, so that it expands (e.g., when pulled from the first end) easily.

In some variations, pushing the proximal end region of the external portion of the flexible tube comprises pushing the intermediate catheter distally to push the proximal end region of the external portion of the flexible tube distally while pulling the puller proximally, wherein the flexible tube is not attached to the intermediate catheter.

In any of the apparatuses and methods described herein, the flexible tube may be unattached to the intermediate catheter. For example, the second end of the flexible tube may be loose.

In any of the methods and apparatuses described herein, a vacuum may be applied through the puller. Thus, the apparatus, and particularly the puller, may be adapted to include a lumen or passage for applying suction. This suction may be used to pull the clot out from the flexible tube once it has been all or partially engulfed, e.g., by the flexible tube.

In general, any of the methods described herein may include capturing the clot within the flexible tube as the puller is pulled proximally.

For example, a method of removing a clot from a vessel may include: advancing an inverting tube thrombectomy apparatus through a vessel until a distal end of the inverting tube thrombectomy apparatus is proximate to the clot, wherein the inverting tube thrombectomy apparatus comprises an intermediate catheter, an inversion support catheter within a lumen of the intermediate catheter, a puller within a lumen of the inversion support catheter, and a flexible tube having a first end coupled at a distal end region of the puller, wherein flexible tube inverts over a distal end of the inversion support catheter and an external portion of the flexible tube extends proximally over the inversion support catheter; positioning the puller and inversion support catheter adjacent to the clot; forming slack in the external portion of the flexible tube; and pulling the puller proximally so that the external portion of the flexible tube rolls and inverts over the distal end of the inversion support catheter so that the slack in the external portion of the flexible tube is withdrawn into the inversion support catheter.

In any of these methods pulling the puller proximally may comprise withdrawing all or a majority of the slack into the inversion support catheter before a second end of the flexible tube is moved distally over the inversion support catheter. For example, pulling the puller proximally may comprise withdrawing the slack into the inversion support catheter while applying 1 pound or less of force (e.g., applying 0.75 or less pounds of force, applying 0.5 pounds or less of force, applying 0.4 pounds or less of force, applying 0.3 pounds or less of force, applying 0.25 pounds or less of force, applying 0.2 pounds or less of force, applying 0.1 pound or less of force, etc.) proximally against the distal end of the inversion support catheter.

In any of the methods described herein, pulling the puller proximally may comprise withdrawing the slack into the inversion support catheter without causing the distal end of the inversion support catheter to withdraw from the clot within the vessel. Thus, the methods described herein may prevent the kickback (e.g., separation from the clot) described above.

Forming slack may comprise advancing the intermediate tube distally to push at least part of the external portion of the flexible tube distally to form slack in the external portion of the flexible tube over the inversion support catheter. For example, forming slack may comprise axially compressing the external portion of the flexible tube on the inversion support catheter by driving the second end of the flexible tube distally. Forming slack may include driving a second end of the flexible tube distally without moving the puller proximally.

For example, a method of removing a clot from a vessel may include: advancing an inverting tube thrombectomy apparatus through a vessel until a distal end of the inverting tube thrombectomy apparatus is proximate to the clot, wherein the inverting tube thrombectomy apparatus comprises an intermediate catheter, an inversion support catheter within a lumen of the intermediate catheter, a puller within a lumen of the inversion support catheter, and a flexible tube having a first end coupled at a distal end region of the puller, wherein flexible tube inverts over a distal end of the inversion support catheter and an external portion of the flexible tube extends proximally over the inversion support catheter; positioning the puller and inversion support catheter adjacent to the clot; advancing the intermediate tube distally relative to the pusher to push at least part of the external portion of the flexible tube distally to form slack in the external portion of the flexible tube over the inversion support catheter; pulling the puller proximally so that the external portion of the flexible tube rolls and inverts over the distal end of the inversion support catheter so that the slack in the external portion of the flexible tube is withdrawn into the inversion support catheter; and capturing the clot with the rolling flexible tube to draw the clot into the inversion support catheter.

Any of the methods described herein may include reducing the tension on the flexile tube (and particularly the portion of the flexible tube that rolls and inverts over the distal end of the inversion support catheter). For example, a method of removing a clot from a vessel may include: advancing an inverting tube thrombectomy apparatus through a vessel until a distal end of the inverting tube thrombectomy apparatus is proximate to the clot, wherein the inverting tube thrombectomy apparatus comprises an intermediate catheter, an inversion support catheter within a lumen of the intermediate catheter, a puller within a lumen of the inversion support catheter, and a flexible tube having a first end coupled at a distal end region of the puller, wherein flexible tube inverts over a distal end of the inversion support catheter and an external portion of the flexible tube extends proximally over the inversion support catheter; and positioning the puller and inversion support catheter adjacent to the clot; and pushing a proximal end region of the external portion of the flexible tube distally over the inversion support catheter while pulling the puller proximally so that the external portion of the flexible tube rolls and inverts over the distal end of the inversion support catheter.

In some variations, pushing the proximal end region of the external portion may comprise pushing the intermediate catheter distally to drive the proximal end region of the external portion distally.

Also described herein are apparatuses, including in systems, for removing a clot. For example the apparatus comprising: an intermediate catheter; an inversion support catheter within a lumen of the intermediate catheter; a puller within a lumen of the inversion support catheter; a flexible tube having a first end coupled at a distal end region of the puller, wherein flexible tube inverts over a distal end of the inversion support catheter and an external portion of the flexible tube extends proximally over the inversion support catheter; and a handle coupled to the intermediate catheter and the puller, wherein the handle is configured to, when activated by a control on the handle, automatically advance the intermediate catheter while one or more of: holding the puller fixed or withdrawing the puller proximally as the intermediate catheter is advanced.

The methods and apparatuses described herein may alternatively or additionally include automatic reloading. For example, described herein are apparatuses and methods of using them that automatically reload the flexible tube after it has been inverted and rolled into the inversion support catheter, so that additional (or a different) clot may be captured. Clot that has already been captured within the inverted flexible tube may be removed proximally through the puller (e.g., puller catheter), using a vacuum and/or a wire within the puller. This may allow the device to be repeatedly used to remove clot without requiring the device to be removed from the body. Thus, the apparatus may repeated peck or bite at a clot by repeatedly rolling and inverting the flexible tube into the inversion support catheter, clearing the portion of the clot captured from the flexible tube into the puller, then automatically and/or manually everting the flexible tube back over the distal end and out of the inversion support catheter. In some variations the inversion support catheter may include a narrower inner diameter region near the distal end than more proximal regions, so that the flexible tube within the inversion support catheter may expand outwards slightly more proximally within the inversion support catheter, which may help release the compressed clot from the flexible tube. In some variations, the flexible tube may be lubricious (e.g., coated, etc.) within the inverted configuration (e.g., within the inversion support catheter). The suction through the puller be applied continuously or intermittently. The suction pressure may be monitored to confirm removal of the clot from the flexible tube before re-setting.

For example, described herein are methods of removing clot from a vessel, the method comprising: advancing an inverting tube thrombectomy apparatus through a vessel until a distal end of the inverting tube thrombectomy apparatus is proximate to the clot, wherein the inverting tube thrombectomy apparatus comprises an intermediate catheter, an inversion support catheter within a lumen of the intermediate catheter, a puller within a lumen of the inversion support catheter, and a flexible tube having a first end coupled at a distal end region of the puller, wherein flexible tube inverts over a distal end of the inversion support catheter and an external portion of the flexible tube extends proximally over the inversion support catheter; and positioning the puller and inversion support catheter adjacent to the clot; pulling the puller proximally to roll the external portion of the flexible tube over a distal end of the inversion support catheter so that it inverts and is drawn into the inversion support catheter, capturing clot and pulling clot material into the inversion support catheter; applying a vacuum though the puller to suction the clot proximally through the puller; and pulling a second end of the flexible tube proximally to roll and evert the external portion of the flexible tube over the distal end of the inversion support catheter so that it extends proximally over the inversion support catheter.

In some variations, the method may repeat the step to remove additional clot. For example, the method may include repeating (e.g., cycling) one or more times, the steps of pulling the puller, applying the vacuum and pulling the second end of the flexible tube to remove additional clot material.

In any of these methods, applying the vacuum may comprise turning the vacuum on while or after the puller is pulled proximally. Pulling the second end of the flexible tube may comprise releasing the puller to allow a bias force to pull the second end of the flexible tube proximally.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A illustrates one example of an intermediate catheter ("delivery catheter" or I.C.) that may be used with a mechanical thrombectomy apparatus as described herein.

FIGS. 1B-1C2 illustrate components of a mechanical thrombectomy apparatus (also referred to herein as an inverting tube thrombectomy apparatus); FIG. 1B shows an example of an elongate inversion support catheter that is configured to include a plurality of slots (shown here as transverse slots) arranged along the catheter in order to enhance flexibility of the elongate inversion support catheter while providing sufficient column strength to resist buckling as the tractor tube is drawn proximally to invert. The slot pattern of FIG. 1B is intended as a single example only. Other slot/cut-out patterns may be used. FIGS. 1C1 and 1C2 show a flexible tubes attached to a puller (e.g., puller catheter in FIG. 1C1, or puller wire in FIG. 1C2). The flexible tubes are shown attached at a first end to a distal end region of the puller; in FIG. 1C1 the puller is a puller catheter (PMC) while in FIG. 1C2 the puller is a guidewire. The flexible tube is shown schematically and may be a knitted, woven, or braided material.

FIG. 2A shows the assembled apparatus in which the flexible tube is coupled to the puller and within the elongate inversion support catheter with the flexible tube inverting over the distal end of the elongate inversion support catheter. FIG. 2B shows the apparatus of FIG. 2A delivered within a vessel near a clot. FIG. 2C shows the operation of the apparatus to withdraw the clot by pulling proximally on the flexible tube from within the elongate inversion support catheter so that the flexible tube is pulled to roll over and evert from the inverted configuration on the outside of the distal end of the elongate inversion support catheter into the un-inverted configuration within the elongate inversion support catheter, pulling the clot with it.

FIG. 3A is an example of a preloaded assembly of an inverting tube thrombectomy apparatus including an intermediate catheter that may be used as described in order to the apparatus though a tortious vessel to a clot location. In this example, all of the other components of the inverting tube thrombectomy apparatus (elongate inversion support catheter) may be held within the intermediate catheter (and may be locked in this position) until deployed, while the pusher (e.g., PMC) and flexible tube are partially extending distally. A guidewire may also be used.

FIG. 3B shows the inverting tube thrombectomy apparatus of FIG. 3A with the inversion support catheter advanced distally.

In FIG. 4A, the inverting tube thrombectomy apparatus is positioned adjacent to the clot. In FIG. 4, in the tortious anatomy, once the puller is pulled proximally to invert the flexile tube (also referred to herein as the tractor tube) over the distal end of the inversion support catheter, the inverting tube thrombectomy apparatus, and particularly the inversion support catheter, may compress, causing the distal face of the flexible tube and the elongate support catheter to pull away from the clot. In a tortious anatomy, such as shown in FIGS. 4A-4B, it may be particularly difficult to advance the apparatus back to the clot (and forward), particularly while the puller pulling the flexible tube over the distal end of the inversion support catheter applies a proximal force against the inversion support catheter.

In FIG. 4C the inverting tube thrombectomy apparatus (e.g., the distal face of the puller, attached flexible tube and/or inversion support catheter) is positioned adjacent to the clot. In FIG. 4D the puller is withdrawn proximally, rolling the flexible tube over the distal end of the inversion support catheter and into the lumen of the inversion support catheter. In this example, pulling the flexible tube over the distal end moves the distal end away from the clot.

FIGS. 5A-5L illustrate one example of a method of operating an inverting tube thrombectomy apparatus to remove a clot that alleviates the tension (compressive force) applied by pulling the flexible tube over the distal end opening of the inversion support catheter, preventing the separation of the inverting tube thrombectomy apparatus from the clot. In this example, the method includes forming slack in an external portion of the flexible tube prior to pulling the puller proximally to roll the flexible tube and invert it over the distal end face of the inversion support catheter.

FIGS. 6A-6C illustrate an example of a method for removing a clot using an inverting tube thrombectomy apparatus that prevents pull back of the end of the inverting tube thrombectomy apparatus from the clot. In this example, the method includes reducing tension in flexible tube as it is rolled and inverted over the distal end of the inversion support catheter by introducing slack (in this example, compressing the flexible tube) prior to rolling and inverting the flexible tube over the distal end face of the inversion support catheter.

FIGS. 7A-7B illustrate an example of a method of removing a clot using an inverting tube thrombectomy apparatus that prevents pull back of the end of the inverting tube thrombectomy apparatus from the clot. In this example, the method includes coordinating pushing the second (unattached) end of the flexible tube distally (e.g., by pushing on the intermediate catheter) and pulling the puller proximally.

In FIG. 8, the inverting tube thrombectomy apparatus includes the flexible tube (e.g., a woven tube) a puller, and an inversion support catheter; a return bias (e.g., in this example, a coil spring) is attached to the second end of the flexible tube to reset the flexible tube on the outside of the inversion support catheter after it is rolled and inverted into the inversion support catheter and released.

FIG. 10A schematically illustrates an example of an inverting tube thrombectomy apparatus that includes a self-biased flexible tube that is coupled to an outer region of the inversion support catheter. FIG. 10B shows an example of an embodiment of the inverting tube thrombectomy apparatus including a self-biased flexible tube configured as a stacked braid.

DETAILED DESCRIPTION

Figure 2A:
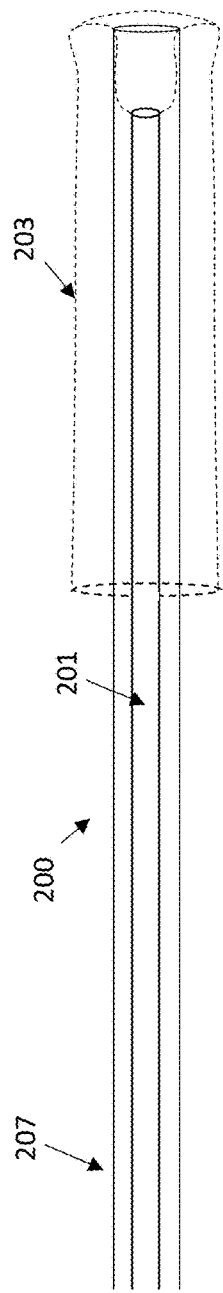
FIGS. 2A-2C illustrate the operation of an inverting tractor mechanical thrombectomy apparatus (e.g., inverting tube thrombectomy apparatus) as described above.

In general, described herein are inverting tube thrombectomy apparatus having a flexible tube, configured as an inverting flexible tube or an inverting tractor tube ("tractor tube") that may be pulled proximally to invert over and into the distal end of an elongate inversion support catheter. An end of the tractor tube may be coupled to a puller (e.g., pull wire, pull catheter, etc.) to provide the proximal pulling force. In particular, described herein are apparatuses and methods of using them that improve or enhance the ease of use, including tracking of the apparatus within a tortious vessel to remove a clot by rolling the flexible tube into the elongate inversion support catheter and grabbing the clot.

In general, the apparatus described herein may be configured to prevent compression of the apparatus (e.g., the inversion support catheter) when pulling the puller to roll and invert the flexible tube into the inversion support catheter, which may separate the distal end of the apparatus from the clot and may make it difficult to advance the apparatus to engage with the clot, particularly in a tortious vessel. Any of the apparatuses described herein (and methods of using them) may be adapted to prevent tension in the flexible tube in the region of the flexible tube that is rolling and inverting over the distal end of the inversion support catheter. For example, tension may be reduced in the region of the flexible tube (the external portion of the flexible tube) by pushing from the second, usually loose or unattached, end of the flexible tube on the outside of the inversion support catheter. The flexible tube may be pushed by a member, including a dedicated wire, rod, etc., or by an outer or intermediate catheter. In some variations, the method may include pushing the end (e.g., the second end, opposite from the first end attached to the puller) of the flexible tube distally to form a slack region.

FIGS. 1A-C2 and 2A-2C illustrate examples of inverting tube thrombectomy apparatus and methods of operating them to remove a clot, respectively.

An inverting tube thrombectomy apparatus for removing a clot from a vessel may be a system, assembly or device including an inversion support catheter having a distal end and a distal annulus (distal end opening), and a flexible tube assembly (which may be referred to as a tractor tube or tractor tube assembly) including a flexible tube coupled to an elongate puller that is positioned within the elongate inversion support catheter. The flexible tube is configured to roll and invert over the distal end opening of the elongate inversion support catheter when pulled proximally by the puller. Knitted tractor tubes are of particular interested and described herein, although it should be understood that other tractor tubes, e.g., woven, braided, etc., may be used.

Tracking of any of the inverting tractor mechanical thrombectomy apparatus described herein may include an intermediate catheter (I.C.) as a delivery catheter along with a guidewire. For example, FIG. 1A illustrates an example of a typical intermediate catheter 101. Note that in some variations an intermediate catheter is not needed or used and the inverting tractor mechanical thrombectomy apparatus may be delivered to the deployment site near the clot to be removed without the need for an intermediate catheter.

FIG. 1B illustrates one example of an inversion support catheter. In this example, the elongated inversion support catheter 103 is formed of a normally high column-strength material (such as a metal, e.g. Nitinol) having a number openings (e.g., cut-out regions) or slots along the length to provide enhanced flexibility. The distal end of the elongate inversion support catheter is open 105. Either the entire length or a portion of the length may be cut/slotted as described. The elongate inversion support catheter includes a catheter body having a distal end region that includes a distal end opening 105. The distal end region may have an increasing softness (measured by durometer, e.g., shore durometer) except that the very distal-most end region (distal end 105, including the distal end opening) may be substantially less soft than the region immediately proximate to it. Thus, although the distal tip region of the catheter (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

In FIG. 1B, the elongate inversion support catheter is an elongate hollow catheter having a column strength that is sufficient to prevent buckling when the catheter is pulled over the distal annulus (distal end opening). Thus, the elongate inversion support may be configured so that it does not collapse (e.g., buckle) when 500 g or less of compressive force is applied (e.g., able to withstand at least about 500 g, at least about 700 g, at least about 600 g, at least about 500 g, at least about 400 g, at least about 300 g, etc. of compressive force) for neurovascular applications. For peripheral vascular applications the elongate inversion support may be selected or configured to withstand at least 1500 g of compressive force (e.g., at least about 2000 g, 1900 g, 1800 g, 1700 g, 1600 g, 1500 g, 1400 g, etc. of compressive force). In general, any of the apparatuses described herein may include an elongate inversion support catheter that is not a full-length catheter, but may include a portion of a catheter, typically at the distal end, connected to a rod, wire, hypotube, or the like. In FIG. 1B the catheter 103 of the elongate inversion support catheter may be any appropriate type of catheter or portion of a catheter, including microcatheters appropriate for neurovascular use.

The inversion support catheter may be solid (e.g., may not include the cuts/slots shown in FIG. 1B).

In some variations the distal end 105 of the elongate inversion support catheter is adapted so that the tractor may slide or roll and invert over the distal end of the catheter without being caught (binding, jamming) or without substantial friction. For example, in some variations the distal tip (end) may be curved or radiused, particularly on the outer surface (e.g., the transition from outer diameter to inner diameter).

FIG. 1C1 shows an example of a flexible tube 111 coupled to a puller 113, forming a pullable tractor assembly 140. In this example, the tractor tube 111 is shown integrated with the puller 113 and extending back over the puller. The puller in this example is a catheter (e.g. a micro catheter, also referred to herein as a PMC or pull micro catheter). In this example, the opposite end of the flexible tractor tube 111 is open and free (e.g., not connected to the puller or catheter, e.g. elongate inversion support catheter, intermediate catheter, etc.). This open, free, end may be adapted to be expanded and held open, e.g., by shape setting back on itself and/or by including an annular bias, to enhance deployment and positioning of the catheter between the flexible tractor tube and the puller. In FIGS. 1C1 and 1C2, the tractor tube is formed of material (e.g., wove, knitted, braided, etc.) that is flexible and elongate. The flexible tube 111 is shown extended from the puller in a first configuration. The relaxed outer diameter of the flexible tractor in this first configuration may have a greater outer diameter than the outer diameter of the catheter of the elongate inversion support into which the tractor will be positioned prior to inverting, or it may be approximately the same. The flexible and tubular tractor 111 may be sufficiently soft and flexible (e.g., having a low collapse strength) so as to easily roll and fold over the distal aperture of the elongate inversion support. The tractor 111 may be configured, e.g., by shape-setting (heat setting, etc.), to expand in the relaxed first configuration to a radial diameter that is between 1.1 and 10 times (e.g., between 1.1× and 5×, between 1.1× and 4×, etc.) the diameter of the inner diameter of the catheter of the elongate inversion support when unconstrained. In FIG. 1C2, the tractor tube 111 is shown coupled to a guidewire (non-hollow structure) 115. The tractor may be formed of a mesh, braided, woven, knitted, or sheet of material and is generally adapted to grasp the object to be removed (e.g., blood clot).

The flexible tubes (e.g., tractor tubes) described herein generally comprises a flexible tube of material that inverts over itself as it rolls over a distal end opening of an elongate inversion support. The flexible tube may be formed of a knitted material, and may be configured (e.g., sized, oriented, etc.) to roll smoothly over the distal end opening of the elongate inversion support catheter. The flexible tube may be configured so that it is doubly biased, in order to prevent jamming and to grab and compress relatively large clots as it rolls and inverts into the elongate inversion support catheter at the distal end opening of the elongate inversion support catheter; the flexible tube may be biased so that it has an expanded (e.g., relaxed) un-inverted configuration having an outer diameter that is approximately the same or slightly larger than the inner diameter of the elongate inversion support catheter, which may be referred to as a second configuration of the flexible tube. The flexible tube may also be further biased so that it has an expanded (e.g., relaxed) inverted configuration (which may be referred to as a first configuration) having an inner and outer diameter that is larger than the outer diameter of the elongate inversion support catheter. The inner diameter in this first configuration may be greater than 1.2× (e.g., between 1.2× and 10×, between 1.2× and 8×, between 1.2× and 6×, between 1.2× and 5×, between 1.2× and 3×, etc.) the outer diameter of the inversion support catheter. Thus, when the flexible tube is placed in and over the distal end of the inversion support catheter, a first (inner) portion of the tractor tube is within the distal end of the elongate inversion support catheter in the un-inverted configuration and it is biased to expand towards (and in some configuration against) the inner diameter of the inversion support catheter; the region of the flexible tube that is inverted over the distal end opening of the inversion support catheter and extends proximally down the outside of the inversion support catheter is in an inverted configuration in which the inner diameter of the flexible tube is biased to be larger than the outer diameter of the inversion support catheter. This double-biased configuration may be a result of the weave pattern (e.g., knitting), and/or a shape setting of the material forming the tractor tube, which may be a shape memory material. As a result, the inverting portion of the flexible tube, where it rolls an inverts over itself at the distal end of the inversion support catheter may be prevented from collapsing on itself as the tractor tube is rolled and pulled into the inversion support catheter. In some variations this configuration may also result in a somewhat flattened (e.g., and in some cases "trumpet shaped") distal end face that is rolling over the distal end opening of the elongate inversion support catheter. The trumpet-shaped distal end may have a teardrop-shaped cross-section. In some variations, the distal end face of the flexible tube may be T-shaped.

Also described herein are variations in which the first configuration of the flexible tube on the outside of the inversion support catheter (which may be referred to herein as an elongate inversion support catheter) maybe flush or nearly flush with the outer diameter of the inversion support catheter, e.g., within 50%, 40%, 30%, 20%, etc. of the outer diameter of the inversion support catheter.

The flexible tube may be coupled to a puller that is within the lumen of the inversion support. The puller may be a wire, filament, rod or more preferably a catheter or tube (and may be referred to herein as a pull micro catheter or "PMC" for convenience). A guidewire may be passed through the flexible tube, and therefore through the inversion support and the tractor tube. As will be described herein, this may be used for positioning.

The inversion support catheter may be configured as a catheter having a distal end opening into which the tractor inverts. The flexible tube may invert and rolls back into itself and may be drawn into the inversion support in a conveyor-like motion; the outward-facing region rolls around to become an inward-facing region, e.g., within the lumen of the inversion support catheter. The rolling motion may thus draw a clot or other object within a vessel into the inversion support. The inversion support catheter may be shaped or configured to have a sufficient column strength to withstand the compressive pulling force of the flexible tube as it is drawn (and rolled, inverting) into the distal end of the inversion support catheter. The inversion support catheter may be slotted (e.g., may include a plurality of slots or openings) to provide increased flexibility as well as column strength. However, as will be described herein, many inversion support catheters may become less flexible (e.g., more rigid) when a compressive force is applied to the flexible tube, either as a result of pulling the flexible tube proximally, either from within the inversion support catheter, or from the outside of the inversion support catheter as the flexible tube brushes against the vessel and/or a delivery catheter when being driven distally towards a clot.

The methods and apparatuses described herein may be used with any of the apparatuses and methods described, for example, in U.S. application Ser. No. 15/291,015, filed on Oct. 11, 2016 ("Mechanical Thrombectomy Apparatuses and Methods") and U.S. application Ser. No. 15/496,570, filed on Apr. 25, 2017 ("Anti-Jamming and Macerating Thrombectomy Apparatuses and methods"), previously incorporated by reference in their entirety.

The inverting tube thrombectomy apparatus (e.g., a mechanical thrombectomy apparatus) may be inserted through a vessel such as a blood vessel, artery, etc., until a distal end, or a distal-most end, of the inverting tube thrombectomy apparatus is proximate to a clot. The clot may be immediately adjacent to the end of the apparatus, or it may be within a few cm (e.g., within 1 cm, within 2 cm, within 3 cm, within 4 cm, etc.). This may be detected by visualization, such as fluoroscopy. Thus the apparatuses described herein may include one or more markers for visualization. Contrast may be used to visualize the clot and/or may be released from the apparatus. The apparatus may be deployed in a pre-loaded/pre-assembled configuration, as will be described in more detail below.

In any of these methods described herein, the flexible tube may be knitted and/or the apparatus may be configured with the opening into the vacuum lumen (e.g., through the puller catheter) at the distal-most end of the device, so that the flexible tube extends behind (proximal) the distal-facing end of the puller catheter. For example, the method of removing a clot from a vessel may include: advancing an inverting tube thrombectomy apparatus through a vessel until a distal end of the inverting tube thrombectomy apparatus is proximate to a clot, wherein the inverting tube thrombectomy apparatus comprises an intermediate catheter, an inversion support catheter within a lumen of the intermediate catheter, a puller catheter within a lumen of the elongate support catheter, and a knitted tube having a first end coupled at a distal end region of the puller catheter, wherein knitted tube inverts over a distal end of the inversion support catheter and extends proximally between the intermediate catheter and the inversion support catheter, further wherein the knitted tube comprises a filament that is knitted to form a plurality of interlocking loop stitches; advancing the puller catheter distally so that a distal face of puller catheter extends distally from the inverting tube thrombectomy apparatus further than the knitted tube; applying a vacuum through the puller catheter to engage the clot with the distal face of the puller catheter; and pulling the puller catheter proximally to roll the knitted tube over a distal end of the inversion support catheter so that the knitted tube inverts over the distal end of the inversion support catheter, captures the clot, and pulls the clot proximally into the inversion support catheter.

The second end of the flexible tube may comprise a cuff that is less flexible that a region of the tube adjacent to the cuff. As will be described in more detail below, the cuff may be formed as a material attached to or applied onto/over the end of the flexible tube. For example, the second end of the flexible tube may comprise a cuff formed of a polymeric material applied onto/over the knitted tube. The cuff may be slit or cut (e.g., all or partially along its length) to provide some flexibility when pulling over or around the end of the tube. For example, the cuff may include longitudinal slits along its length. The cuff may have a durometer that is greater than the durometer of the flexible tube (e.g., knitted tube). The cuff, in some variations, is thicker than the flexible tube. In any of the variations described herein, the cuff may be radiopaque (e.g., by including a radiopaque material, such as platinum) on or within the cuff.

Figure 2B:
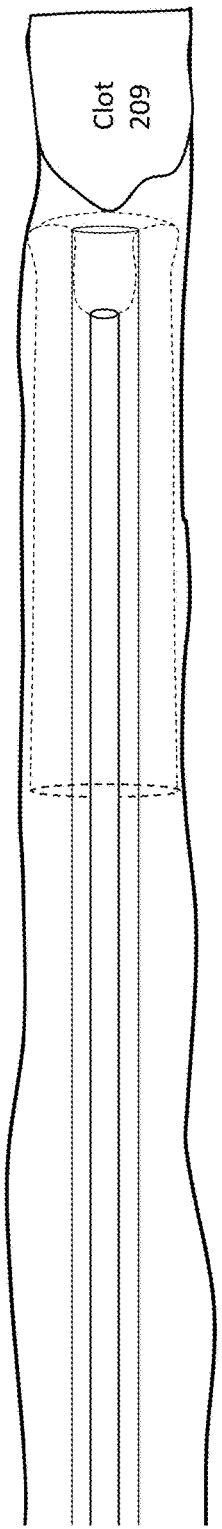
Figure 2C:
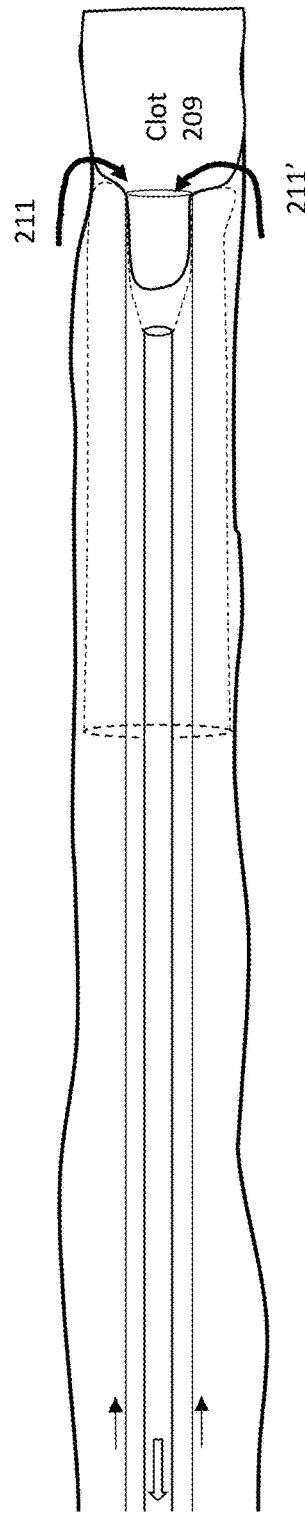

FIG. 2A illustrates an example of a deployed inverting tube thrombectomy apparatus 200. In FIG. 2B the inverting tractor mechanical thrombectomy apparatus is shown deployed near a clot 209 within a vessel. In the deployed configuration the puller 201 (shown here as a puller micro catheter) is held within the elongate inversion support catheter so that the flexile tube 203 extends from the end of the puller and expands toward the inner radius of the elongate inversion support catheter 207; at the distal end opening of the elongate inversion support catheter the flexible tube inverts over itself and extends proximally in an inverted configuration over the distal end of the elongate inversion support catheter. As shown in FIG. 2C, by pulling the puller proximally, the flexible tube may roll and invert over the distal end opening of the elongate inversion support catheter, drawing the adjacent clot into the elongate inversion support catheter, as shown.

FIG. 2A the inversion support catheter is positioned between the flexible tube and the puller so that the flexible tube can be pulled proximally by pulling on the puller and rolling the flexible tube into the elongate inversion support catheter so that it inverts. The portion of the flexible tube that is inverted over the distal end of the elongate inversion support catheter has an outer diameter that is greater than the outer diameter of the elongate inversion support catheter. In some variations the diameter (e.g., inner diameter) of the external portion of the flexible tube outside of the inversion support catheter may be approximately the same diameter (e.g., within 1.01× and 1.3×) of the outer diameter of the inversion support catheter. In some variations, the flexible tube may be biased so that it has a relaxed expanded configuration with a diameter that is greater than the outer diameter (OD) of the elongate inversion support catheter; in addition, the flexible tube may also be configured (e.g., by heat setting, etc.) so that when the flexible tube is inverted and rolled over the distal end opening into the elongate inversion support catheter, the inverted flexible tube within the elongate inversion support catheter has an outer diameter that is greater than the inner diameter of the elongate inversion support catheter (e.g., greater than 0.1×, 0.5× 0.6×, 0.7×, 0.75×, 0.8×, 0.9×, 1×, etc. the inner diameter, ID, of the elongate inversion support catheter. This combination of an un-inverted diameter of the flexible tube of greater than the diameter of the OD of the elongate inversion support catheter and an inverted diameter of the flexible tube of greater than about 0.7× the ID of the elongate inversion support catheter is surprisingly helpful for preventing jamming of the apparatus, both when deploying the apparatus and when rolling the flexible tube over the distal end opening of the elongate inversion support catheter to grab a clot. The flexible tube may be expandable and may be coupled to the puller as shown. In some variations the flexible tube and the puller may comprise the same material but the flexible tube may be more flexible and/or expandable, or may be connected to elongate puller (e.g., a push/pull wire or catheter).

In FIG. 2C the clot may be drawn into the elongate inversion support catheter by pulling the flexible tube proximally into the distal end of the elongate inversion support catheter, as indicated by the arrows 211, 211' showing pulling of the inner portion of the flexible tube, resulting in rolling the flexible tube over the end opening of the catheter and into the catheter distal end and inverting the expandable distal end region so that it is pulled into the catheter, shown by arrows. The end (e.g., the second end) of the flexible tube outside of the catheter may be "loose" relative to the outer wall of the catheter.

In general the inverting tube thrombectomy apparatuses described herein may be highly flexible, both before actuating and during operation. For example, the flexible tube may not increase the stiffness/flexibility of the catheter of the elongate inversion support, and particularly the distal end region of the catheter too much, to avoid impacting maneuverability, particularly within tortious vessels of the neurovasculature. Described herein are flexible tubes portions that increase the stiffness of the last y cm (e.g., distal most 20 cm, 18 cm, 15 cm, 12 cm, 10 cm, 9 cm, 8 cm, 7 cm, 6 cm, 5 cm, 4 cm, 3 cm, 2 cm, 1 cm, etc.) of the catheter less than a predetermined percentage (e.g., less than 10%, 12%, 15%, 18%, 20%, 25%, 30%, etc.). For example, described herein are flexible tube portions that pass through the catheter and double back over the distal end of the catheter but increase the stiffness of a distal 5 cm of the catheter by less than 15% of the stiffness of the distal 5 cm of the catheter without the flexible tube extending therethrough and doubling back over the distal end of the catheter.

As mentioned, the flexible tubes may be woven, braided and/or knitted materials. For woven and braided materials, which may include a plurality of fibers that are woven or braided to form the inverting tube, these structures may be tuned to prevent jamming and/or to reduce the force necessary to pull the flexible tube and invert over the catheter tip. For example, the mechanical atherectomy apparatus may include a braid-type flexible tube that can roll freely around the tip of catheter even in a tortuous anatomy and when grabbing clot by tuning one or more of the braid structure; minimizing the braid angle; including a hydrophilic coating on the distal aspect of the catheter outer diameter (OD) or the inner diameter (ID) of the braid (e.g., flexible tube); including a radiused wall on the catheter; and/or increasing the stiffness of the distal tip region relative to adjacent proximal regions. Alternatively it may be advantages to have a hydrophilic coating on 1, 3, 5, 10, or 15 cm of the distal ID or the entire catheter ID. This may even enhance aspiration of the clot without a tracking element.

As mentioned, the flexible tube (e.g., braided, woven, knitted, etc.) may be configured to collapse down into the inner diameter (ID) of the catheter as little as possible. For example the flexible tube may collapse to an ID that is greater than, equal to, or within 90%, 85%, 75%, 70%, 65%, 60%, or 50% of the catheter inner diameter (ID)/Catheter Tip OD, since, when the flexible tube is being pulled around catheter tip it may create axial tension on the flexible tube (e.g., braid, knit, etc.) that can inadvertently cause the flexible tube to jam on the catheter tip. When flexible tube is pulled around catheter tip, the flexible tube is being pulled in the axial orientation creating axial tension on flexible tube structure as the flexible tube is being pulled through the catheter ID. By having the flexible tube elements jam at an ID greater than or equal to 90%, 85%, 75%, 70%, 65%, 60%, or 50% of the catheter ID (or in some variations, OD), when being axially tensioned, the flexible tube is less likely to grab/synch down onto the catheter tip, helping the braid roll around the catheter tip with less axial force applied by the user. If less axial force is required by the user to pull the flexible tube structure around the tip then the catheter tip is less likely to buckle or deflect when retracting the flexible tube. It may be advantageous to minimize the chance the catheter tip will buckle. The flexible tube can be tuned to "jam" at a specific ID by controlling any of the following variables and in any combination: selecting a specific number of braid ends, selecting the size/diameter of the braid ends; selecting the braid material (e.g., multifilament or monofilament); heat setting the bias on the braid (e.g., braid diameter); and selecting a braid pattern, e.g., 1×2, 1×1 or any other pattern.

The braid angle may be minimized to prevent locking up of the rolling of the flexible tube over the catheter end opening. Typically, the lower the braid angle (e.g., 45 degrees or less, 40 degrees or less, 35 degrees or less, 30 degrees or less, 25 degrees or less, 20 degrees or less, etc.) the less likely it is to have the braid cross over points catch on the catheter tip.

In any of the variations described herein, the catheter and/or a surface of the flexible tube may be coated to enhance rolling over the distal end region of the catheter. It may be helpful to have a hydrophilic coating on the distal aspect of the catheter OD or the ID of the flexible tube so the flexible tube can more easily side over the catheters distal end and around the tip of the catheter when pulled through the inside of the catheter.

The radius wall of the catheter tip may be chosen/set to within a range that allows sliding. For example, it may be helpful for the tip of the catheter to have the largest radius possible but at least 0.0025" radius wall on the catheter, ideally approximately 0.005" radius wall.

The stiffness of the distal of the elongate inversion support catheter may be sufficiently stiff to prevent collapse as the flexible tube is pulled; it may also be lubricious (e.g., by a coating or material property). The distal most section of the elongate inversion support catheter tip (e.g., the last 5 mm) may be fabricated of a material which is stiff enough and lubricious enough so the distal tip of the catheter does not collapse or buckle inward ward when the braid structure is rolling around the catheter tip. Thus, the distal tip may have a stiffness that is greater than the more proximal region at the distal end of the catheter.

It may be helpful or desirable to have pores in the flexible tube. A lack of gaps or small pore size may limit the ability of the braid to grab clot. Alternatively or additionally, it may be desirable to form a braid structure with texture. One example is to braid two or more different diameter braid ends into the same structure: the difference in braid end diameters will help form a texture to the braid structures outer surface, aiding the grabbing of the clot when rolling the braid-dozer around the catheter tip.

As an alternative (or in addition) the flexible tube may be configured to lock so it does not compress in diameter during axial load by adding a coating, laminate or adhesive to the braid at a desired diameter. Adding a thin coating, laminate or adhesive can inhibit the braid elements from sliding with respect to each other, thereby locking the braid to a specific diameter. The coating can be applied while leaving the majority of the pores and pore area substantially open. Examples of thin coatings include urethanes and silicones with and without hydrophilic coatings and hydrophilic coatings with no tie layer.

FIG. 3A shows one example of a pre-loaded inverting tube thrombectomy apparatus for removing a clot from a vessel that may be delivered through a tortious anatomy. In this example, the apparatus may include an intermediate catheter 303 having a distal end 305. The intermediate catheter (I.C.) may be considered part of the inverting mechanical thrombectomy apparatus, although in other variations it may be considered a separate component that is used with the inverting mechanical thrombectomy apparatus. The apparatus also includes an elongate inversion support catheter 307 within the lumen of the intermediate catheter. The elongate inversion support catheter 307 has a distal end 311 and a distal end opening. The apparatus also includes a puller 319 extending distally within the elongate inversion support catheter and a flexible tube 315 extending proximally from a distal end region of the puller. The puller extends from the distal end of the intermediate catheter and the distal end opening of the elongate inversion support catheter.

In the configuration shown in FIG. 3A, the elongate inversion support catheter is held within the lumen of the intermediate catheter so that the distal end opening of the elongate inversion support catheter is proximal to the distal end opening of the intermediate catheter by a first distance 325. This distance may be between about 1 mm and about 10 cm (e.g., between about 2 mm and about 10 mm, between about 2 mm and about 20 mm, between about 2 mm and about 30 mm, etc.). The elongate inversion support catheter may be fixed in position relative to the intermediate catheter, so that as the two move together, until released. For example, the proximal ends of the intermediate catheter and the elongate inversion support catheter may be removably coupled.

The flexible tube in the pre-assembled apparatus of FIG. 3 extends between the elongate inversion support catheter and the intermediate catheter for some second distance along the length 323 of the elongate inversion support catheter. Securing the end of the flexible tube between the I.C. and the distal end of the elongate inversion support catheter may help both hold it in place, so that the flexible tube may be pushed formed (e.g., in compression). For example, the second length 323 may be between about 1 mm and about 50 cm (e.g., between about 5 cm and about 10 cm, between about 1 cm and about 20 cm, between about 1 cm and about 10 cm, between about 2 cm and about 20 cm, between about 2 cm and about 10 cm, etc.).

The portion of the flexible tube 315 and puller 319 (e.g., pull micro catheter, or pmc) in this pre-loaded example may extend distally and ride over the guidewire 317. The flexible tube and puller may also be longitudinally fixed relative to the intermediate catheter 303 (e.g., by releasably locking, e.g., at the distal end region) or they may be somewhat longitudinally slideable (and, in some variations, prevented from exceeding a range of, e.g., between about 1 mm and 20 cm from the distal end opening 305 of the intermediate catheter.

In this example, the portion 327 of the flexible tube 315 that extends outside of the intermediate catheter 303 may be between about 1 mm and about 20 cm (e.g., between about 1 cm and about 7 cm, between about 1 cm and about 10 cm, between about 1 cm and about 15 cm, between about 2 cm and about 10 cm, between about 2 cm and about 7 cm, etc.). As mentioned, this distance may be fixed (e.g., by fixing the puller with respect to the push catheter and/or I.C.), or variable. In any of these variations, the puller may extend some distance 329 beyond the distal attachment site for the flexible tube, or the flexible tube may be attached at the distal end of the puller. The distance from the attachment site of the flexible tube and the distal end of the puller may be between about 0 mm and about 10 cm, for example (e.g., between about 1 mm and about 10 cm, between about 1 mm and about 5 cm, etc.).

FIG. 3B shows the apparatus of FIG. 3A, but with the inversion support catheter 307 advanced distally. In this example, the distal opening 311 of the inversion support catheter 307 has been pushed distally toward the attachment site of the flexible tube, and any clot. Once in position, the puller may be pulled proximally to invert the flexible tube into the inversion support catheter.

Flexible Tubes Having Slack

Figure 4A:
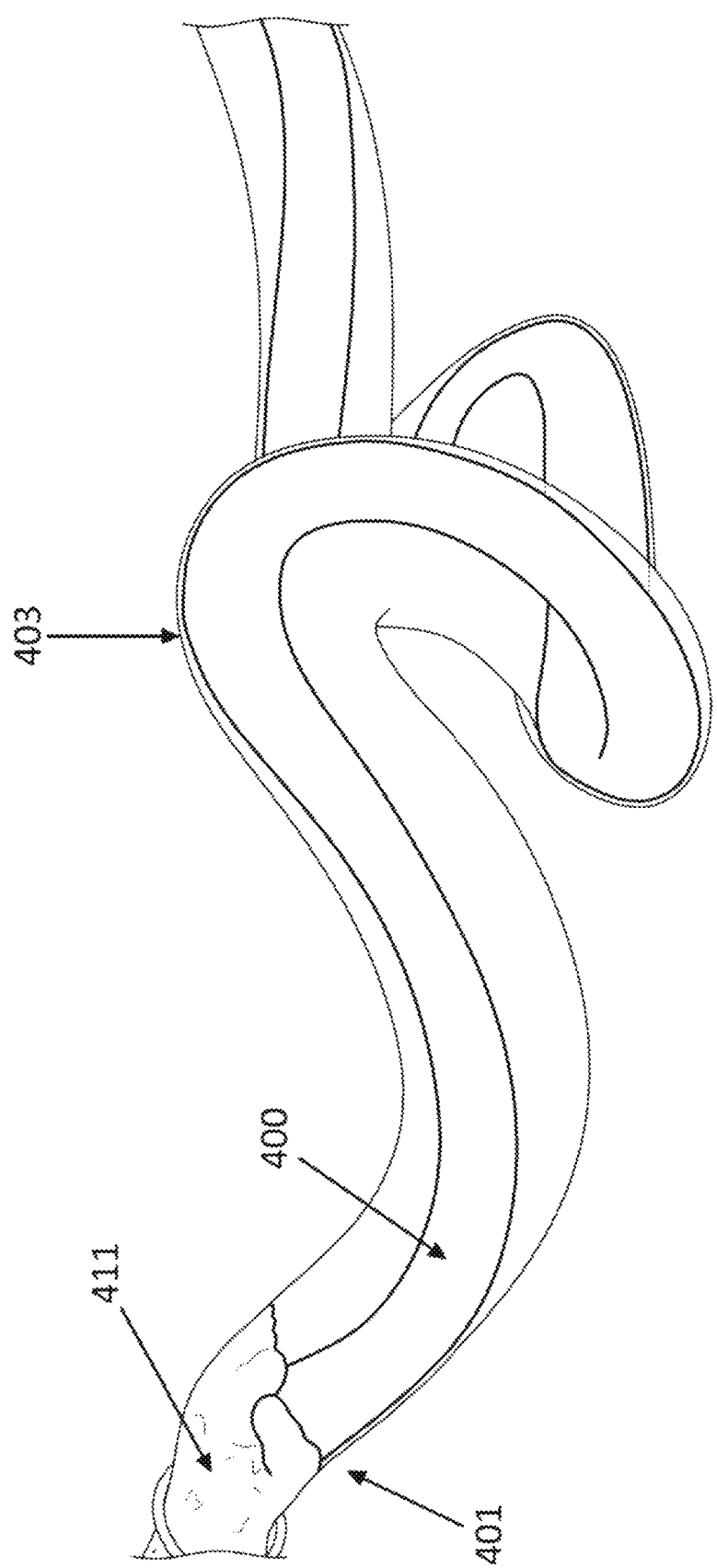
FIGS. 4A-4B illustrate one example of an inverting tube thrombectomy apparatus within a tortious anatomy that may pull away from the clot when deploying the flexible tube (e.g., when rolling the flexible tube over the distal end and into the inversion support catheter.
Figure 4B:
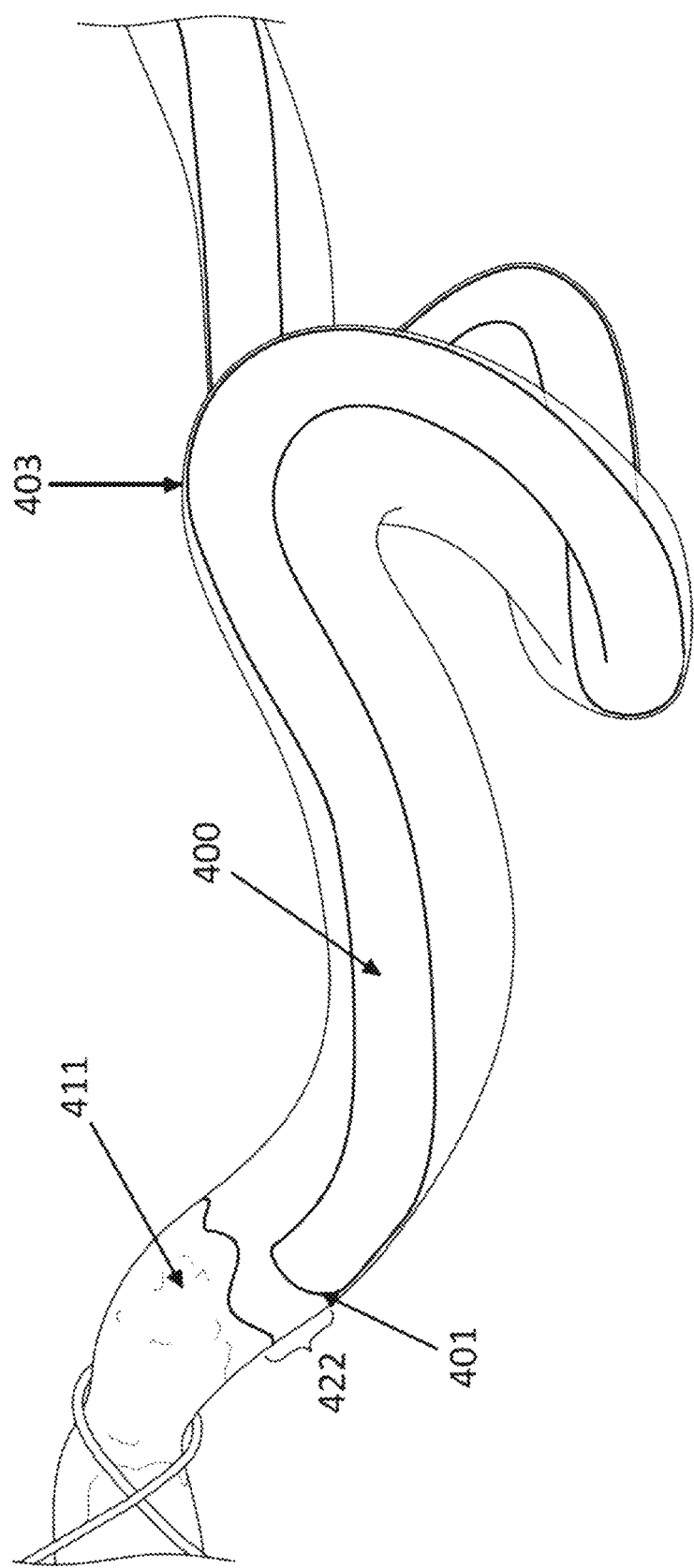

FIGS. 4A-4B and 4C-4D illustrate kickback when using an inverting tube thrombectomy apparatus. For example, in FIG. 4A, a model of a tortious vessel 403 (e.g., a neurovascular region) is shown; the vessel is transparent to show a clot 411 and an inverting tube thrombectomy apparatus 400 that has been positioned with the distal end 401 adjacent to the clot. This example of an inverting tube thrombectomy apparatus includes a puller with a flexible tube attached near the distal end, and an inversion support catheter, The puller extends within the lumen of the inversion support catheter and the flexible tube extend from within the lumen of the inversion support catheter, out of the distal end of the inversion support catheter where it everts over itself to extend proximally along the outside from the distal end of the inversion support catheter. The second end of the flexible tube may be held between the outer surface of the inversion support catheter and an inner surface of an intermediate catheter, or it may be fully released from intermediate catheter. When positioned next to the clot 411 in FIG. 4A, the distal end of the catheter and therefore the inverting face of the flexible tube, may be positioned next to the clot. Pulling the puller proximally will roll and invert the flexible tube (the outer portion of the flexible tube) over the distal end of the inversion support catheter. However, as shown in FIG. 4B, the force applied by the flexible tube pulling proximally against the inversion support catheter (even a high column-strength inversion support catheter as shown in FIG. 1B) may compresses the distal end of the inversion support catheter slightly, and/or may causes it to separate from the clot. In FIG. 4B, the same device after pulling the puller proximally is shown with the distal end separated slightly from the clot (space 422). This compressive force may also make additional distal tracking of the deployed device difficult within the tortious vessel.

Figure 4D:
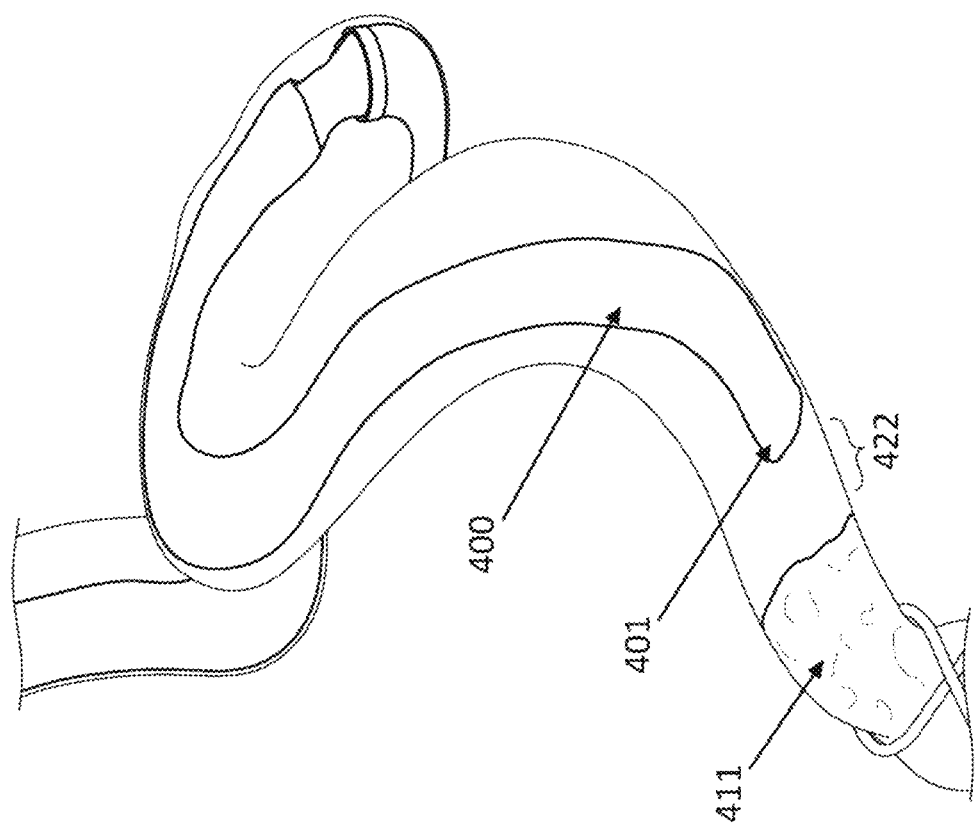
FIGS. 4C and 4D illustrate another example of the 'kickback' that may occur in an inverting tube thrombectomy apparatus which may be difficult to correct for in a tortious vessel.
Figure 4C:
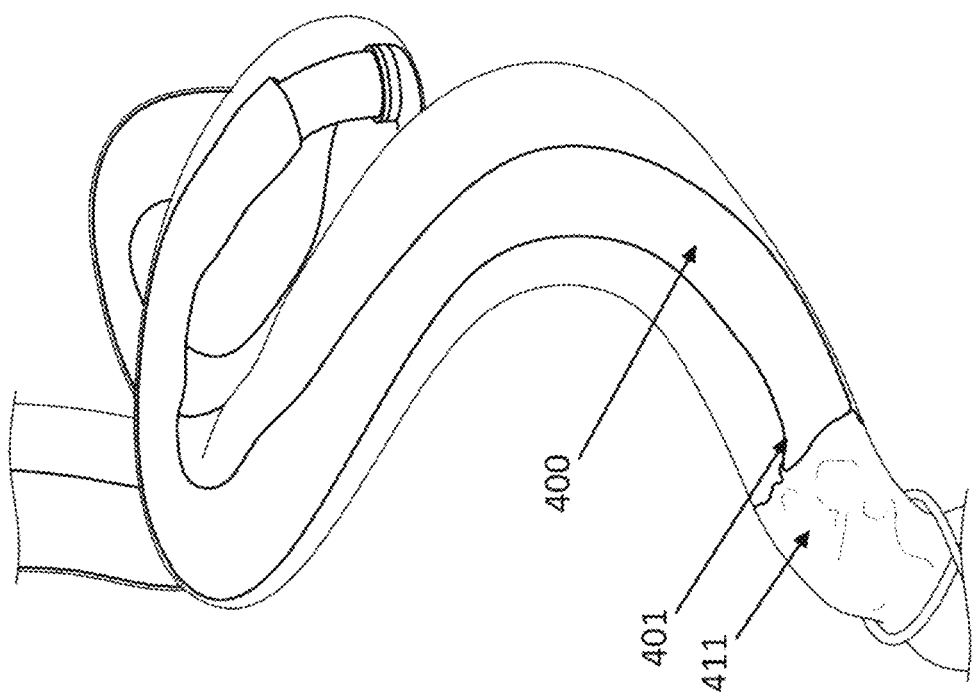

FIGS. 4C and 4D illustrate another example of this. In FIG. 4C the distal end 401 of the inverting tube thrombectomy apparatus 400 is adjacent to the clot 411. Pulling the puller proximally to roll and invert the flexible tube into the inversion support catheter may pull the distal end of the inverting tube thrombectomy apparatus 400 away from the clot 411, as shown in FIG. 4D, introducing a gap 422.

Figure 5E:
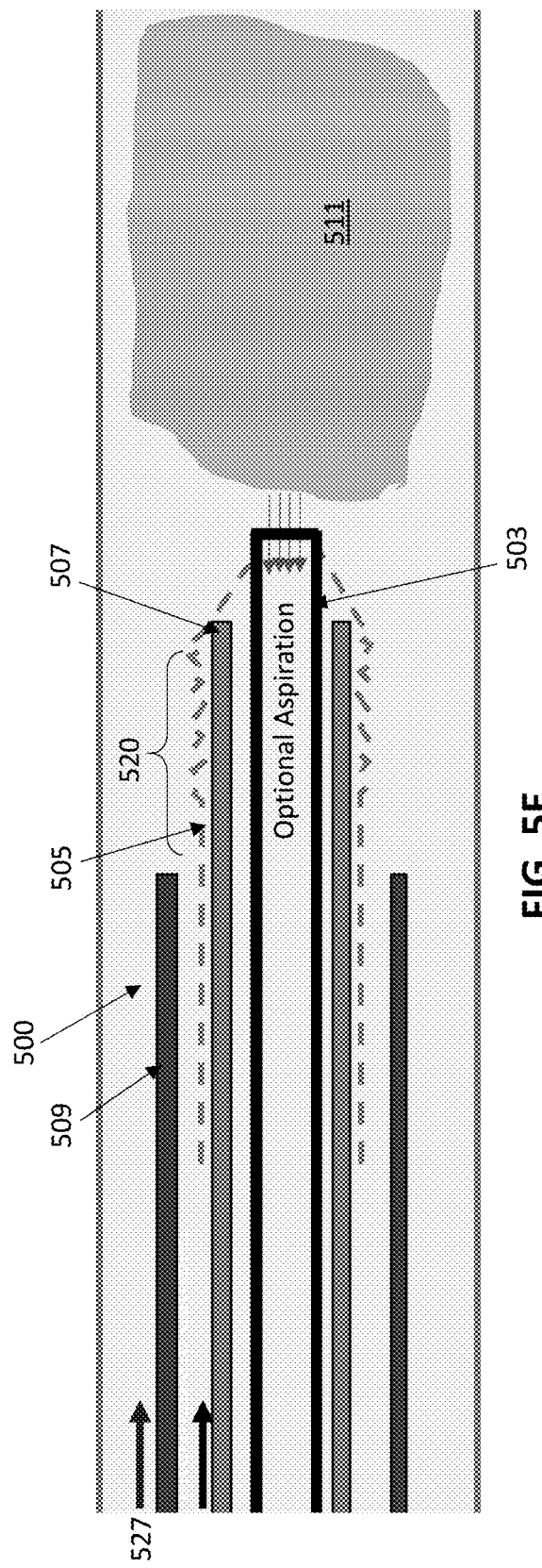

In order to prevent this kickback, the tension on the flexible tube may be reduced or eliminated. For example, FIGS. 5A-5L illustrate one example of a method of removing a clot that reduces or eliminates the tension on the portion of the flexible tube that is rolling and inverting over the distal end of the apparatus. In FIG. 5A, a sectional view through an inverting tube thrombectomy apparatus is shown. The inverting tube thrombectomy apparatus includes a puller 503 (shown as a puller catheter) with a flexible tube 505 (e.g., a woven tube, knitted tube, etc.) attached near the distal end, and an inversion support catheter 507. The puller extends within the lumen of the inversion support catheter and the flexible tube extend from within the lumen of the inversion support catheter, out of the distal end of the inversion support catheter where it everts over itself to extend proximally along the outside from the distal end of the inversion support catheter. The second end of the flexible tube may be held between the outer surface of the inversion support catheter and an inner surface of an intermediate catheter 509, as shown. In FIG. 5A, the apparatus may be tracked over a guidewire 513 to be positioned adjacent to a clot 511. Thus, the apparatus may be pre-loaded with an intermediate catheter to the face of a clot. In FIG. 5B, the inversion support catheter 507 may be advanced distally towards the clot, as shown by arrow 521. The intermediate catheter 509 may then be pulled back, as shown by the arrow 524 in FIG. 5C to completely or partially unsheathe the flexible tube 505, exposing the outer portion of the flexible tube over the inversion support catheter 507. For example, in some variations the intermediate catheter may be pulled back is 30-95% of the length of the flexible tube 505.

Figure 5F:
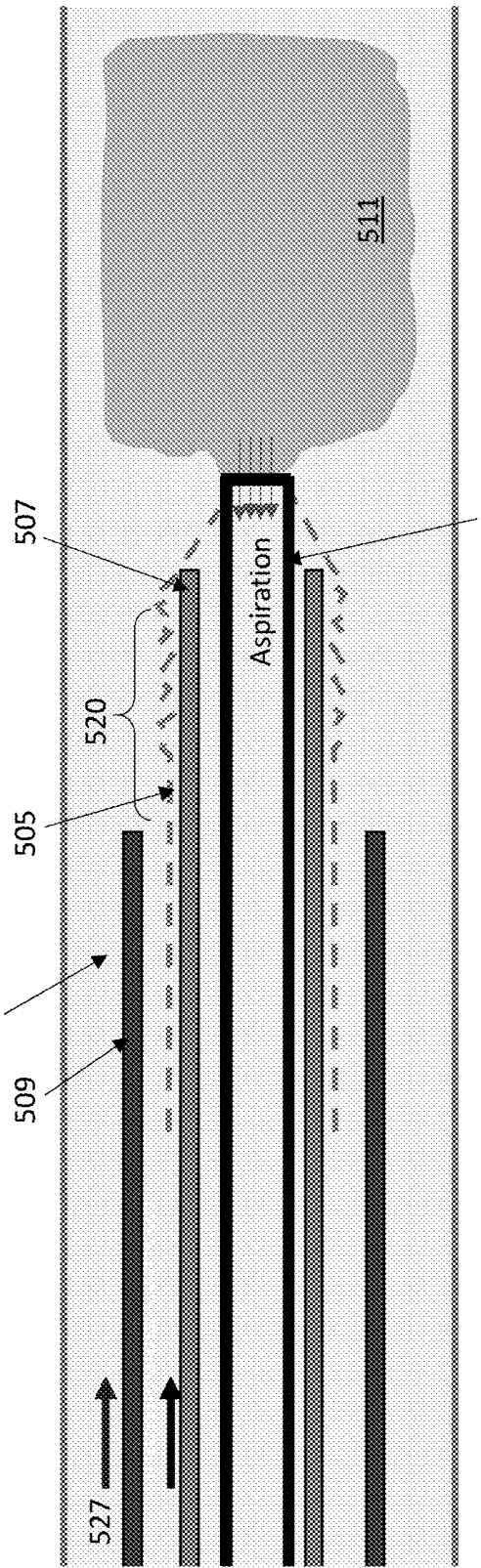

To prevent kickback when inverting the flexible tube, slack 520 may be added to the outer portion of the flexible tube, as shown in FIG. 5D. In this example, slack 520 (shown as a bunching up of the flexible tube on the outside of the inversion support catheter before the distal end) may be added to the flexible tube by pushing the intermediate catheter distally 526 (e.g., approximately 50% of the exposed length of the flexible tube, e.g., the outer flexible tube region). In woven flexible tubes, this may compress the weave. Thereafter, the device may be operated, e.g., by pulling the puller, to roll and invert the flexible tube and grab clot. For example in FIG. 5E, the guidewire is first removed, and aspiration (e.g., vacuum) may be applied through the lumen of the puller (and/or the inversion support catheter) to connect to the clot. The apparatus may also be additionally tracked distally slightly, to capture the clot 511 as shown in FIG. 5F. For example, when aspiration is being applied, the apparatus 500 may be advanced 527 (the intermediate catheter, inversion support catheter and/or puller, all or some of which may be locked together proximally) distally until flow through the puller stops, indicating that the clot is on the puller (e.g., "corked"), as shown in FIG. 5F.

Figure 5K:
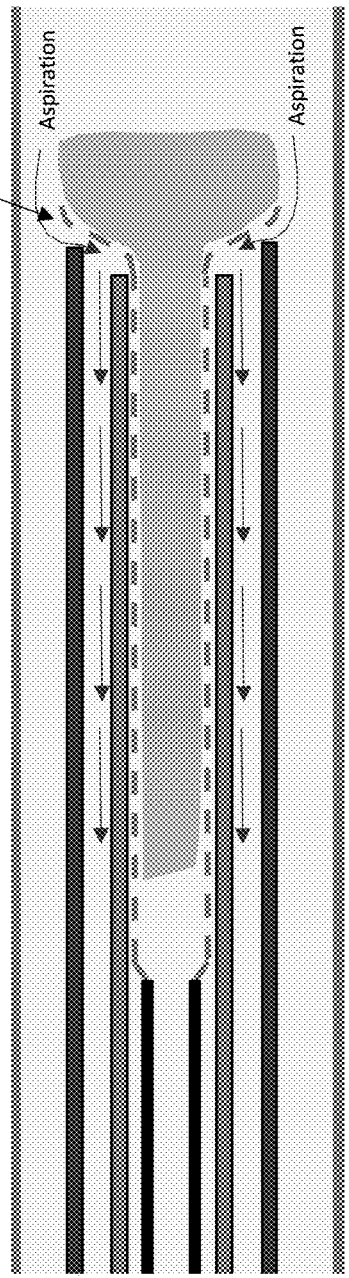
Figure 5L:
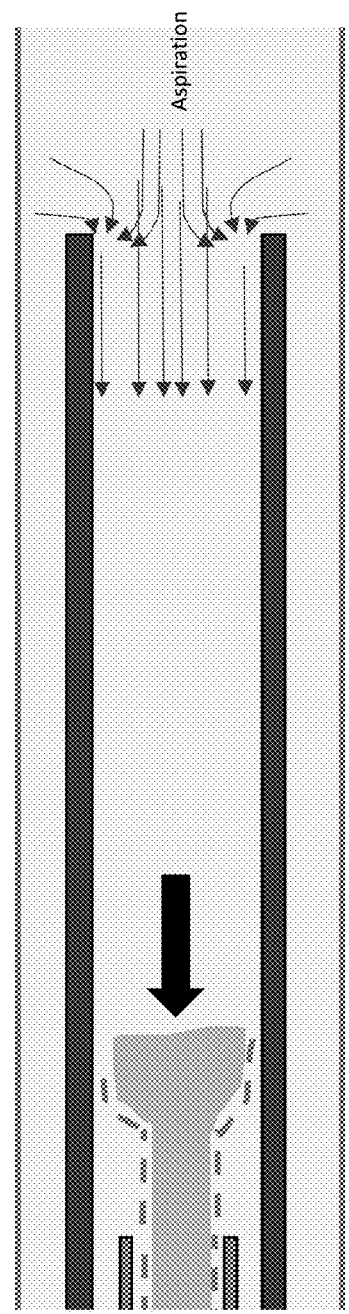

Once positioned, the puller may be pulled proximally 532 while advancing the inversion support catheter and intermediate catheter (together), as shown in FIGS. 5G-5J, to capture clot. Additional slack may be added during this process by, for example, advancing the intermediate catheter independently of the rest of the device; alternatively or additionally, the flexible tube may be released from between the intermediate catheter and the inversion support catheter, as shown in FIG. 5I. As shown in FIGS. 5K and 5L, the clot may be removed fully into the inversion support catheter and/or the intermediate catheter (as shown in FIG. 5L) by withdrawing first the puller and then the rest of the apparatus proximally, while applying aspiration (e.g., suction) through the intermediate catheter.

FIGS. 6A-6C illustrate another example of a method of removing a clot while preventing kickback by releasing tension on the flexible tube. In FIG. 6A, an example of an apparatus 600 (similar to that shown in FIG. 5A, above) is positioned adjacent to a clot 603. As described above, before pulling the puller to roll and invert the flexible tube into the inversion support catheter, the outside region of the flexible tube may be compressed to form slack, for example, by advancing the intermediate catheter distally, after partially or completely removing from over the flexible tube, to push the flexible tube distally. Thereafter, in FIG. 6B, the puller may be pulled proximally while advancing the intermediate catheter to capture clot. In FIG. 6C, the intermediate catheter may be fully unsheathed from over the flexible tube, and more of the clot may be ingested by the rolling, inverting flexible tube.

FIGS. 7A-7B illustrate an alternative variation in which the tension on the flexible tube may be reduced or eliminated when rolling and inverting the outer portion of the flexible tube by coordinating the application of both a distal pushing force on the second end of the flexible and a pulling force on the first end of the flexible tube when pulling the puller proximally. In FIG. 7A, the apparatus 700 includes a puller 703 to which the flexible tube 705 is attached near the distal end of the puller. An inversion support catheter 707 is between the puller and the flexible tube, and an intermediate catheter 709 extends over the majority of the length of the apparatus. In FIG. 7A, the apparatus is shown deployed, but prior to rolling/inverting the flexible tube 705. In FIG. 7B, tension that may otherwise apply a compressive force on the distal end of the inversion support catheter may be reduced or eliminated by applying a distal force (e.g., by advancing the intermediate catheter distally 721 in this example) before or while pulling 723 the puller proximally to roll and invert the flexible tube over the distal end. The puller may be pulled slightly faster than the rate at which the intermediate catheter is advanced distally, as the flexible tube may extend slightly within the inversion support catheter.

Automatic Relaoading

Figure 8:
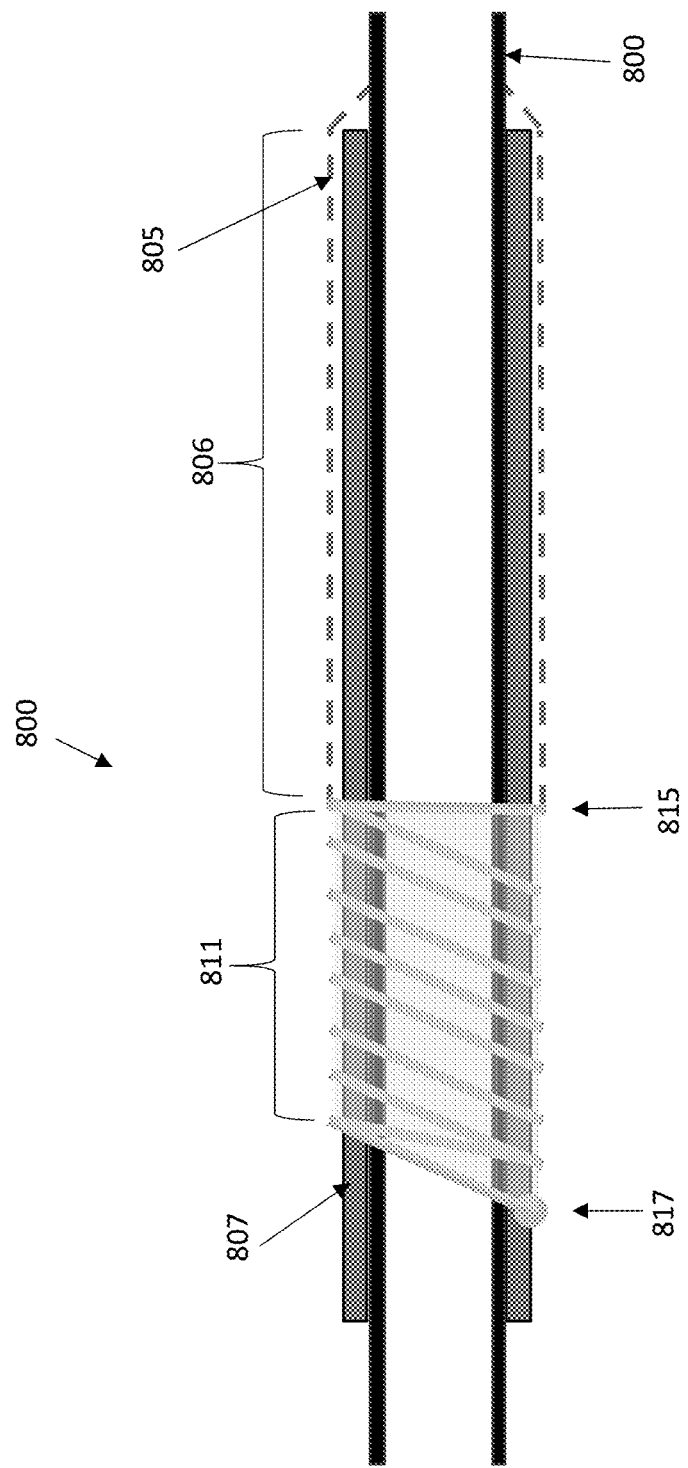
FIG. 8 is an example of an inverting tube thrombectomy apparatus that is configured to automatically reload to remove multiple 'bites' of clot without needing to be removed from within the vessel.

FIGS. 8-11F illustrate apparatuses and methods that automatically reload the flexible tube after grabbing all or a portion of clot. For example, in FIG. 8, the apparatus includes a bias (an external bias) for pulling the flexible tube from within the inversion support catheter back outside of the inversion support catheter (rolling and everting). In FIG. 8, the apparatus 800 includes a puller 803 and a flexible tube (e.g., woven, knitted, etc.). A first end of the flexible tube 805 is attached near the distal end region of the puller. The puller is within the lumen of an inversion support catheter 807, and the flexible tube extends over the outer surface of the inversion support catheter. A region 806 of the flexible tube extends on the outside of the inversion support catheter. The second end (or a region at the second end) of the flexible tube is connected to a bias 811, shown here as a spring element. The spring may be heat set in a compressed configuration, as shown. A distal end of the bias 815 is attached to the second end of the flexible tube (or a cuff, not shown, on the flexible tube). Another, e.g., a proximal end 817, of the spring may be attached to the inversion support catheter 807, as shown.

FIGS. 9A-9D illustrate the operation of an apparatus such as that shown in FIG. 8, which is biased to return the flexible tube to the outside of the inversion support catheter. The amount of bias may be set so that the force applied is relatively low (e.g., pushing the puller distally may allow the flexible tube to reset (e.g., evert and roll back) the flexible tube to the outside of the inversion support catheter; alternatively the bias may be higher, so that the bias resets the flexible tube after just releasing the puller.

Figure 9A:
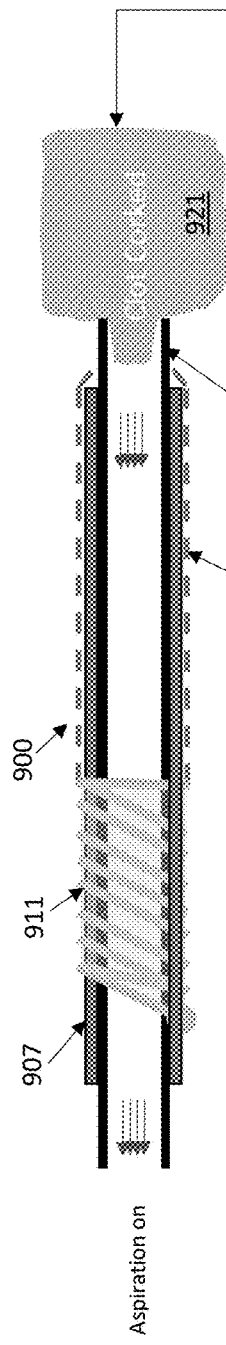
FIGS. 9A-9D illustrate a method of removing a clot including automatically reloading the flexible tube without having to remove it from the vessel.
Figure 9B:
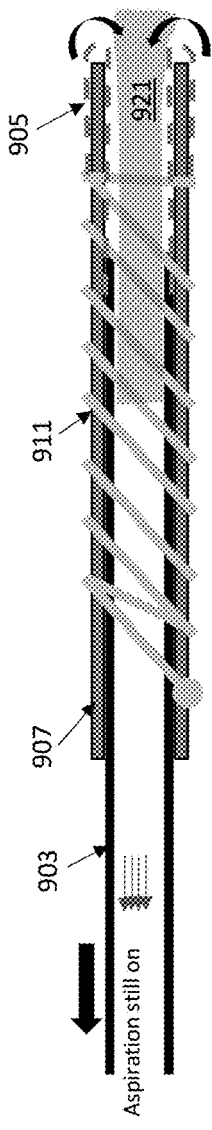
Figure 9C:
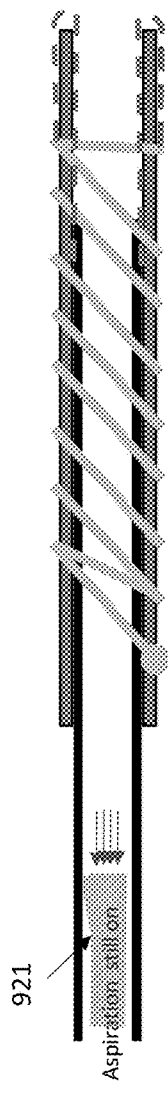
Figure 9D:
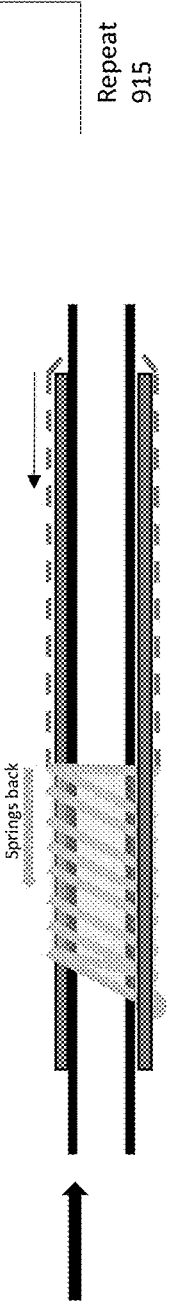

In FIG. 9A, the apparatus 900 may be approximated near the clot and aspiration (e.g., suction) applied through the lumen of the puller 903, as shown, until the clot is attached to the puller ("corked"). The puller 903 may then be pulled proximally, as shown in FIG. 9B, to roll 933 the flexible tube 905 and invert it into the inversion support catheter 907, capturing the clot. Pulling the puller proximally also pulls against the bias 911. The puller may be pulled until it reaches a stop, which may be set by the bias (spring 911) or by a mechanical stop, or both. Once The clot or portion of the clot within the inversion support catheter that has been engulfed by the flexible tube may then be aspirated proximally down the puller, as shown in FIG. 9C. Once cleared from the flexible tube, which may be detected by monitoring the suction through the puller (e.g., showing a drop in suction pressure when the clot is removed proximally from the flexible tube), the flexible tube may be reset outside of the inversion support catheter as shown in FIG. 9D, by applying a small force driving the puller distally, allowing the spring (bias) to evert and roll the flexible tube back out of the inversion support catheter and over the outside surface, as shown. This processes may be repeated 915 as many times as desired; large clots may be removed by taking multiple bites in this manner, or multiple different clots may be removed with the same apparatus. The apparatus shown in FIGS. 8 and 9A-9D may include an intermediate catheter (not shown).

The flexible tube, as described above, may be any appropriate flexible tube. For example, the flexible tube may be a braid (e.g., braid structure). In some variations the flexible tube may be a braid of a flat or round wire that is braided and heat set (as described above, it may be heat set to have an inner diameter in tension that is greater than the outer diameter of the inversion support catheter). For example the flexible tube may be formed as a braid of 144 strands of 0.001" NiTi filaments that are braided at large braid angle (e.g., having a very smooth surface). In some variations, the braid may include a low durometer polymer laminate or covering, on all or braid part of braid length. In some variations, the braid may be configured as a knit structure. The knit may be formed of a round or flat wire having a circular knit structure. The apparatus may be heat set so that the ID of the flexible tube when tensioned is greater than the outer diameter of the inversion support catheter. A knit may include a low durometer polymer laminate or covering, on all or braid part of braid length.

Any appropriate bias may be used. For example, the bias may be a spring such as a metallic or polymeric spring. The spring may be heat set in a closed pitch form. For example, the spring may be a metal or metallic material such as NiTi, Cobalt Cr, stainless steel, etc. The spring may be, e.g., a polymeric tubing spring, such as a spring formed of a silicone, urethane, latex or other elastic material.

In some variations, an additional element, such as a wire, may be used to assist the clot in removing/releasing from the flexible tube. For example, a wire have a bent or bendable distal end may be used to help pull the clot out of the distal end of the puller.

Figure 10A:
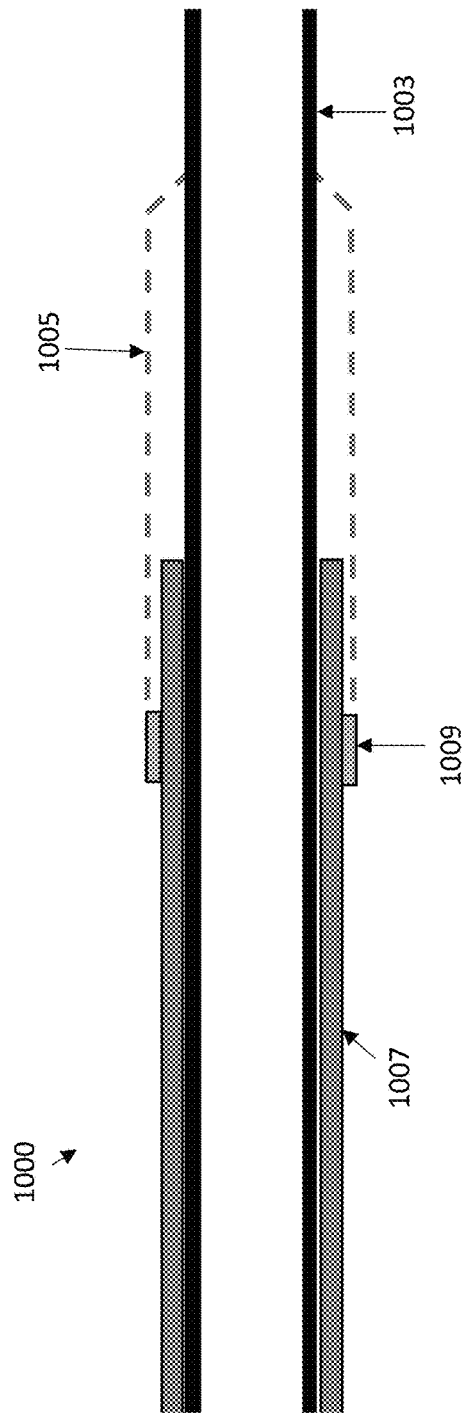
FIGS. 10A-10B show another example of an inverting tube thrombectomy apparatus that is configured to automatically reload to remove multiple 'bites' of clot without needing to be removed from within the vessel.

FIGS. 10A-11F illustrate another example of an apparatus including a bias to restore the flexible tube to the outside of the apparatus. In this variations, the flexible tube is biased to return to the outside of the inversion support catheter. For example, in FIG. 10A, the apparatus 1000 includes a puller 1003 to which a flexible tube 1005 is attached at a first end to the distal end region of the puller. The puller has a relatively large outer diameter (in both this example and the example shown above in FIG. 8), but is slidably held within the inner lumen of the inversion support catheter 1007. In addition, the flexible tube 1005 is attached at the second end to the outside of the inversion support catheter at an attachment region 1009. In FIG. 10A, the flexible tube is biased to spring back to this configuration (e.g., a loading or insertion configuration), in which the flexible tube is outside of the inversion support catheter. In this example the flexible tube is attached proximal to the distal end of the puller; any appropriate distance from the distal end of the puller may be used (e.g., more than 0.1 mm, 0.2 mm, 0.3 mm. 0.5 mm, 1 mm, 2 mm, 3 mm, etc. and/or less than about 0.1 mm, 0.2 mm, 0.3 mm, 0.5 mm, 1 mm, 2 mm, 3 mm, 4 mm, 5 mm, 6 mm, 7 mm, 8 mm, 9 mm, 10 mm, etc.). Alternatively the flexible tube may be attached to the distal end of the puller (e.g., flush with the distal end).

Figure 10B:
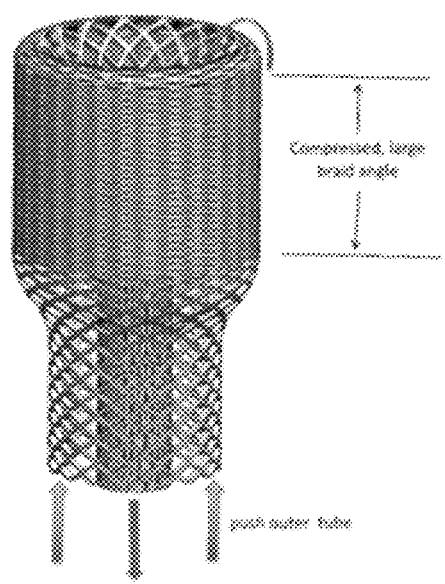

In some variations, the flexible tube is configured as a braid that has a stacked configuration when attached to the outside of the inversion support catheter with the puller distal end aligned with the end of the inversion support catheter. In FIG. 10B, for example, a flexible tube shown as a weave formed of a Nitinol material having a stacked braid configuration is illustrated.

Figure 11A:
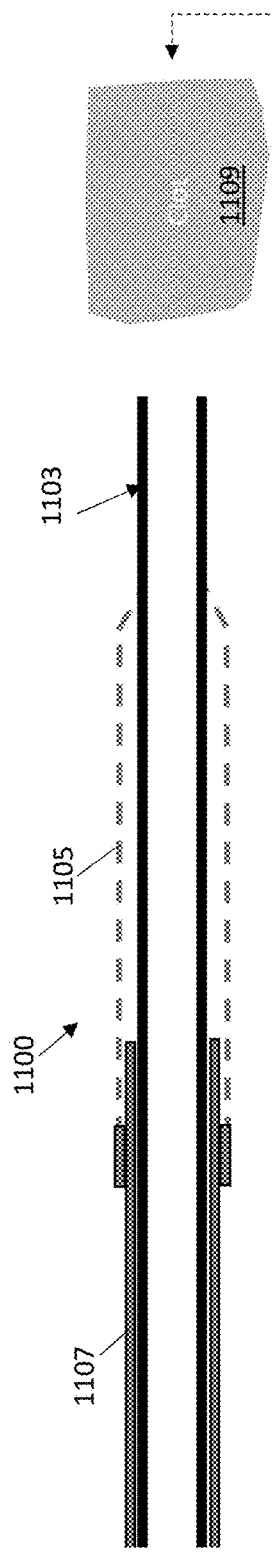
FIGS. 11A-11F illustrate an example of a method of removing clot and automatically reloading the flexible tube without having to remove it from the vessel.
Figure 11B:
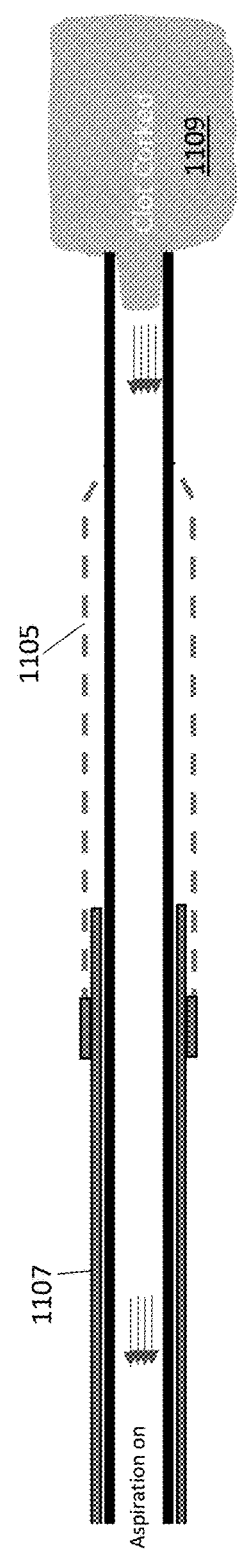
Figure 11C:
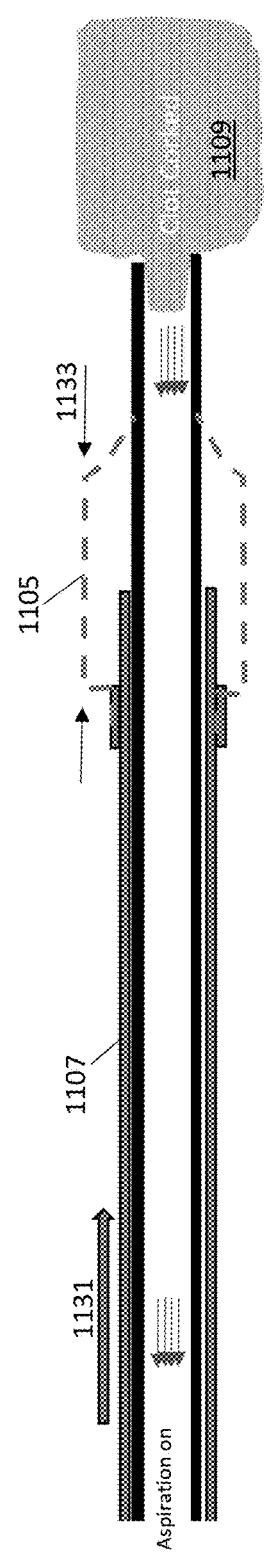
Figure 11D:
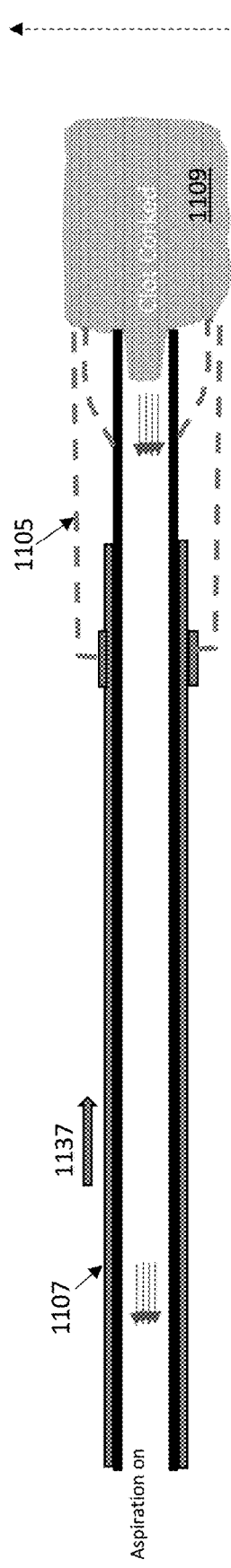
Figure 11E:
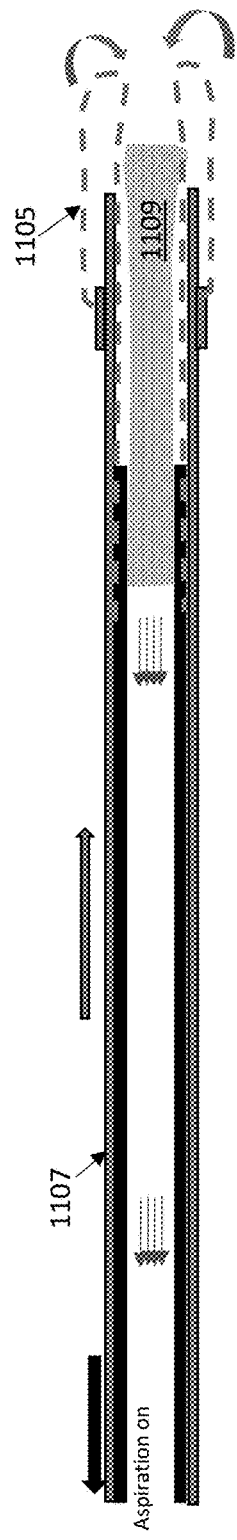

FIGS. 11A-11F illustrate the operation of an apparatus such as the one shown in FIG. 10A. In FIG. 11A, the apparatus is deployed near the clot 1109 with the puller 1103 extended distally ahead of the rest of the apparatus. In FIG. 11B, aspiration may be used to attach the clot 1109 to the puller (shown with the clot "corked" on the distal end of the puller). Thereafter, the inversion support catheter 1107 may be advanced 1131 distally to compress 1133 the weave of the flexible tube 1105, causing it to stack up as shown in FIG. 11C into a stacked configuration. This configuration is equivalent to forming slack in the flexible tube as described above. While (optionally, but preferably) still applying aspiration through the puller, the inversion support catheter 1107 may be advanced distally 1137 (as shown in FIG. 11D), against the clot, and at least partially over it. The inversion support catheter (e.g., the outer catheter) may be advanced distally so that the distal end of the inversion support catheter extends to or past the end of the puller, which may advance the flexible tube over the clot. The inversion support catheter may then be advanced distally while pulling the puller proximally, to roll and invert the flexible tube, as shown in FIG. 11E, to further ingest the clot, as shown. Alternatively the inversion support catheter may be held still while pulling the puller proximally; in some variations the inversion support catheter and puller are moved in a coordinated manner, either together simultaneously or incrementally and alternately.

Figure 11F:
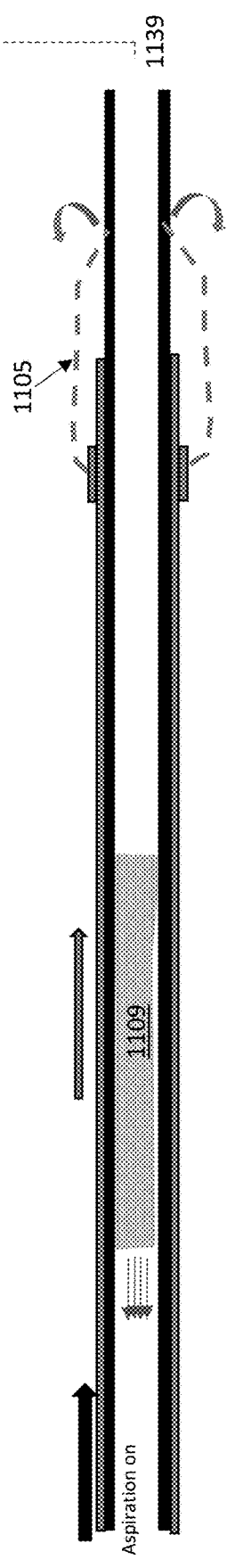

The clot within the puller may be removed proximally (e.g., by aspiration and/or mechanically, such as using a wire), as shown in FIG. 11F. In addition, the puller may be advanced distally to evert and roll the flexible tube back out of the inversion support catheter. This process may then be repeated (shown by dashed arrow 1139) to remove additional clot material. In any of these variations, the clot may be cut after a certain amount of it has entered into the device, e.g., by a separate or integrated cutter (such as a wire, etc.). This may allow repeated bites of clot to be removed using the same device.

Although not shown explicitly in FIG. 11C, the apparatus shown may also include an intermediate catheter, e.g., within which the inversion support catheter (outer catheter) and the puller (pull catheter, inner pull catheter or inner catheter) may move into and/or out of, as shown in FIGS. 5K-5L, above).

Figure 12:
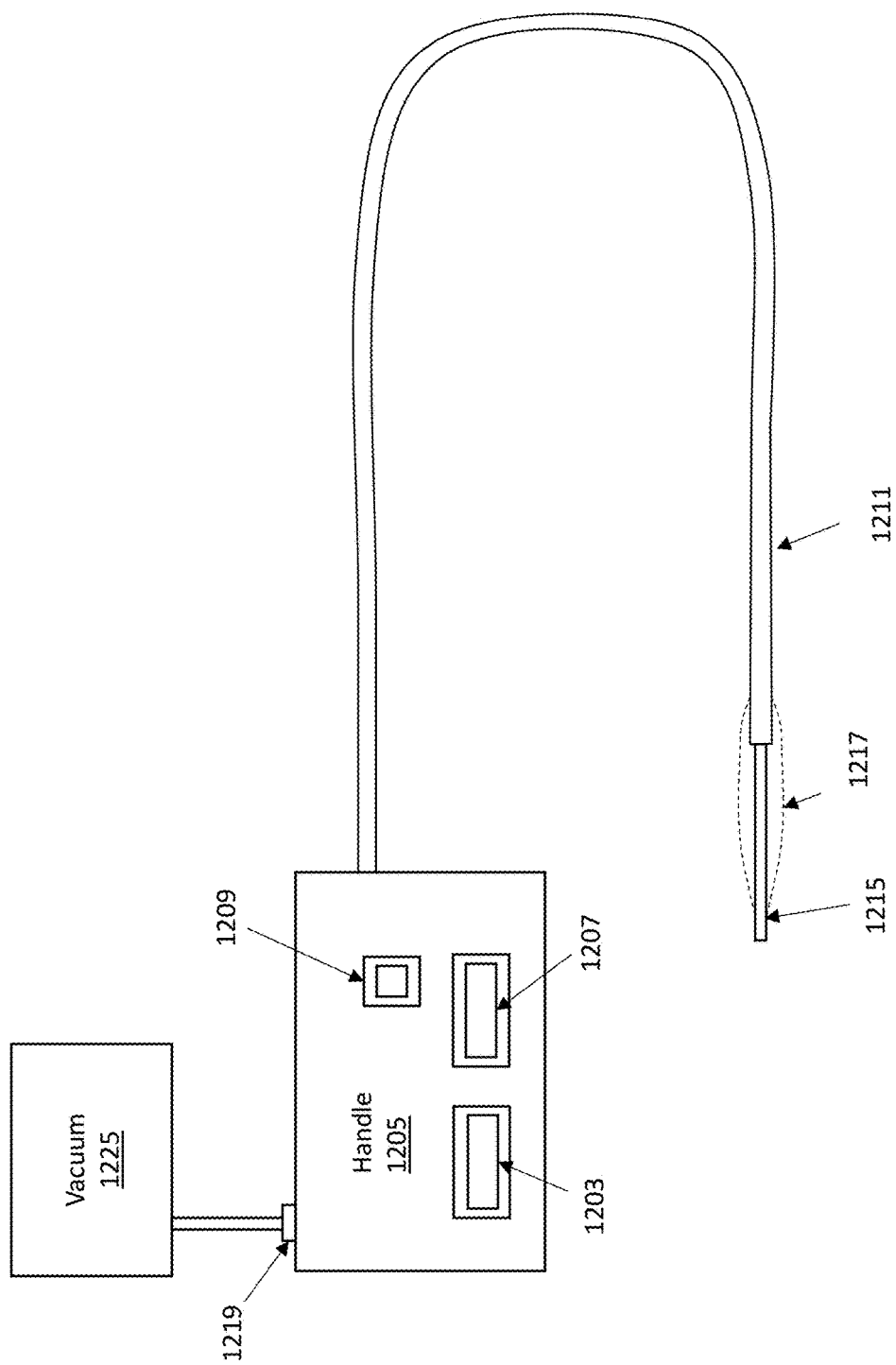
FIG. 12 is a schematic illustration (not to scale) of one variation of an apparatus for removing one or more clot(s) from a vessel. This apparatus may be configured to remove multiple clots by repeatedly withdrawing clot and resetting to an initial position; clot material may be withdrawn through the lumen of the puller catheter (e.g., inner catheter).

FIG. 12 illustrates one example of an apparatus (e.g., a system) for removing a clot, a series of clots and/or multiple clots, as described herein. The schematic shown in FIG. 12 is not to scale. For example, in FIG. 12, the apparatus includes an inversion support catheter 1211 and a puller catheter 1215 within a lumen of the inversion support catheter 1211. The puller catheter, as described above, may have a large inner diameter to allow removal of clot through the puller catheter inner lumen. For example, the inner diameter of the puller catheter may be about 75% (or about 80% or about 85% or about 90% or about 95%) or more than the inner diameter of the inversion support catheter. In some variations the outer diameter of the puller catheter is within 15% or less of the inner diameter of the inversion support catheter (e.g., within 12%, within 10%, within 8%, within 7%, within 5%, etc.). Thus the puller catheter may slide within the inversion support catheter, but may maximize the inner diameter of the inversion support catheter in order to pass clot through the puller catheter.

A flexible tube 1217 is connected to the distal end region of the puller catheter and to an outer surface of the distal end region (or distal end) of the inversion support catheter, as shown. Thus, the flexible tube has a first end coupled at a distal end region of the puller catheter, and a second end coupled at an outer surface of a distal end region of the inversion support catheter. As mentioned above, the flexible tube may be any appropriate material for grabbing clot, such as a woven, knitted or braided material, including metallic woven, knitted and/or braided materials. The flexible tube may be biased or may include a biasing element that is pre-biased to drive the flexible tube to the initial (delivery) configuration, such as shown in FIG. 10A. For example, in some variation the flexible tube includes a shape memory material, such as Nitinol, that is biased to return to the predetermined shape.

In FIG. 12, an intermediate catheter is not shown, but may be included and the inversion support catheter, puller catheter and flexible tube may be passed through the intermediate catheter.

The apparatus shown in FIG. 12 also includes a handle 1205 coupled to the inversion support catheter and the puller catheter. The handle is shown schematically in FIG. 12, but may be shaped for held-held use; alternatively the handle may be part of a base unit that is not hand-held. As shown, the handle includes a vacuum port 1219 that couples to a vacuum 1225, and may couple the vacuum line to a lumen of the puller catheter.

The handle may include one or more controls 1203, 1207, 1209 that may control the operation of the apparatus and particular the relative movement of the puller catheter and the inversion support catheter. The proximal end regions of the puller catheter and the inversion support catheters may be coupled to one or more actuators within the handle (not visible) to drive axial movement (distal/proximal movement) of these members. For example the handle may be configured to, when activated by one or more controls on the handle, advance the inversion support catheter distally before concurrently advancing the inversion support catheter distally while withdrawing the puller catheter proximally, as described in the methods illustrated in FIGS. 11A-11F (and particularly FIG. 11C and FIG. 11D-11E described above). In any of these variations, the handle may be configured to reset the inversion support catheter proximally and the puller catheter distally, e.g., to reset the puller catheter and the inversion support catheter to the delivery configuration. For example, the apparatus may include a control 1209 that may release the inner and/or outer catheters (e.g., the puller catheter and/or inversion control catheter) to allow the device to return to the delivery catheter; alternatively the control may actively move the inner and outer catheters to the delivery configuration.

The handle may be further configured to apply vacuum through the puller catheter while advancing the inversion support catheter distally before concurrently advancing the inversion support catheter distally while withdrawing the puller catheter proximally. For example, the handle may include control logic that applies the negative pressure (e.g., vacuum from the vacuum device 1225) when the actuators within the handle move the inversion support catheter distally while moving the puller catheter proximally. The control logic within the handle may be software, hardware or firmware, and may coordinate operation of the handle. For example the handle may be configured to separately and/or jointly move the inner catheter (puller catheter) and the outer catheter (inversion support catheter), as mentioned above, and/or to coordinate the application of suction (e.g., vacuum) through the puller catheter.

Separate controls on the handle may control the movements involved in the different stages of the operation. For example, the handle may include a first control to advance the inversion support catheter distally and a second control to advance the inversion support catheter distally while withdrawing the puller catheter proximally. Alternatively or additionally, the first control may advance the inversion support catheter distally and may separately advance the inversion support catheter distally while withdrawing the puller catheter proximally. In some variations, the handle is configured to advance the inversion support catheter distally to a predetermined distance (e.g., 1 mm, 2 mm, 3 mm, 4 mm, 5 mm, 1 cm, 1.5 cm, 2 cm, 3 cm, etc.) before advancing the inversion support catheter distally while withdrawing the puller catheter proximally to a variable distance and/or to a second predetermined distance (e.g., 1 mm, 2 mm, 3 mm, 4 mm, 5 mm, 1 cm, 1.5 cm, 2 cm, 3 cm, 4 cm, 5 cm, 6 cm, 7 cm, 8 cm, 9 cm, etc.).

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An apparatus for removing a clot, the apparatus comprising:
   an intermediate catheter comprising an outer surface and an inner surface defining a lumen;
   an inversion support catheter comprising an outer surface and an inner surface defining a lumen, the inversion support catheter being disposed within the lumen of the intermediate catheter;
   a puller disposed within the lumen of the inversion support catheter;
   a flexible tube having a first end coupled at a distal end region of the puller, and a second end held between the outer surface of a distal end region of the inversion support catheter and the inner surface of the intermediate catheter, wherein the flexible tube comprises a slack region formed by a portion of the flexible tube being bunched up on itself on the outer surface of the distal end region of the inversion support catheter, wherein the intermediate catheter is configured to be advanced distally to form the slack region.

2. The apparatus of claim 1, wherein the first end of the flexible tube is coupled proximal to the distal end region of the puller by greater than 0.5 mm.

3. The apparatus of claim 1, wherein the puller is a puller catheter.

4. The apparatus of claim 1, wherein the puller is a wire.

5. The apparatus of claim 1, wherein the flexible tube comprises a woven or knitted material.

6. The apparatus of claim 1, wherein the flexible tube comprises a braided material.

7. The apparatus of claim 1, wherein an outer diameter of the puller is within about 10% of an inner diameter of the inversion support catheter.

8. The apparatus of claim 1, further comprising a guidewire extending through the flexible tube.

9. The apparatus of claim 1, wherein the second end of the flexible tube includes a cuff.

10. The apparatus of claim 9, wherein the cuff is less flexible than a region of the flexible tube adjacent to the cuff.

11. The apparatus of claim 9, wherein the intermediate catheter is configured to be retracted or removed over the flexible tube and then be advanced distally against the cuff to distally drive the flexible tube and form the slack region.

12. The apparatus of claim 1, wherein the flexible tube comprises a woven flexible tube and the slack region comprises compressed weaves.

13. The apparatus of claim 1, wherein an outside region of the flexible tube is configured to be compressed to form the slack region.

14. The apparatus of claim 13, wherein the outside region of the flexible tube adjacent to the first end coupled at the distal end region of the puller is configured to be compressed to form the slack region.

15. The apparatus of claim 1, wherein the intermediate catheter is configured to be advanced distally to axially compress an outside region of the flexible tube to form the slack region.

* * * * *